(12) United States Patent
Inana

(10) Patent No.: US 7,781,205 B2
(45) Date of Patent: Aug. 24, 2010

(54) CARTRIDGE RETAINING MECHANISM FOR NUCLEIC ACID EXTRACTING APPARATUS

(75) Inventor: Katsuya Inana, Asaka (JP)

(73) Assignee: Fujifilm Corporation, Tokyo (JP)

( * ) Notice: Subject to any disclaimer, the term of this patent is extended or adjusted under 35 U.S.C. 154(b) by 726 days.

(21) Appl. No.: 11/794,375

(22) PCT Filed: Feb. 21, 2006

(86) PCT No.: PCT/JP2006/003524

§ 371 (c)(1), (2), (4) Date: Jun. 28, 2007

(87) PCT Pub. No.: WO2006/088258

PCT Pub. Date: Aug. 24, 2006

(65) Prior Publication Data

US 2010/0035336 A1 Feb. 11, 2010

(30) Foreign Application Priority Data

Feb. 21, 2005 (JP) .............................. 2005-043967

(51) Int. Cl.
*C12M 1/34* (2006.01)
*C12M 3/00* (2006.01)
*C12Q 1/68* (2006.01)

(52) U.S. Cl. ........................................ 435/287.2; 435/6

(58) Field of Classification Search ............... 435/6, 435/287.2
See application file for complete search history.

(56) References Cited

U.S. PATENT DOCUMENTS 5,114,858 A * 5/1992 Williams et al. ............ 435/270
6,110,428 A * 8/2000 Borst et al. .................. 422/101
7,429,356 B2 * 9/2008 Seto et al. ..................... 422/63
2004/0235025 A1 11/2004 Mori et al.

FOREIGN PATENT DOCUMENTS

| JP | 2004-113043 A | 4/2004 |
|---|---|---|
| JP | 2004-180637 A | 7/2004 |
| JP | 2004-290149 A | 10/2004 |
| JP | 2005-328730 A | 12/2005 |
| JP | 2006-95499 A | 4/2006 |

* cited by examiner

*Primary Examiner*—Walter D Griffin
*Assistant Examiner*—Lydia Edwards
(74) *Attorney, Agent, or Firm*—Birch, Stewart, Kolasch & Birch, LLP

(57) ABSTRACT

A cartridge retaining mechanism equipped in a nucleic acid extracting apparatus for extracting a nucleic acid, the cartridge retaining mechanism comprising: a cartridge having a cylindrical shape with a bottom, and the bottom is shaped in a funnel shape; a nucleic acid-adsorbing solid carrier that traps a nucleic acid, and the nucleic acid-adsorbing solid carrier is disposed at the bottom of the cartridge; and a cartridge retaining member that retains the cartridge, wherein the cartridge retaining member comprises: a supporting part that supports the cartridge; and a pressure-proof retaining part that is attached to an open end of the cartridge, and wherein the pressure-proof retaining part has a nozzle receiving opening, onto which a pressure nozzle of the nucleic acid extracting apparatus is pressed, and wherein the cartridge is retained between the supporting part and the pressure-proof retaining part upon pressing the pressure nozzle onto the nozzle receiving opening.

6 Claims, 14 Drawing Sheets

CARTRIDGE RETAINING MECHANISM FOR NUCLEIC ACID EXTRACTING APPARATUS

TECHNICAL FIELD

The present invention relates to a retaining mechanism for a cartridge for extracting a nucleic acid equipped in a nucleic acid extracting apparatus for automatically extracting a nucleic acid from a sample solution containing the nucleic acid.

BACKGROUND ART

An automatic nucleic acid extracting system automatically extracting DNA and RNA is being proposed for post-genome researches (for example, in Japanese Patent Application No. 2004-148365 below).

FIG. 15 is a schematic illustration showing an automatic nucleic acid extracting system.

The automatic nucleic acid extracting system 100 has a cartridge holder 103 retaining plural cartridges 104 in an aligned state, a pressure nozzle 101 for feeding pressurized air to the cartridges 104, and a moving head retaining the pressure nozzle 101 and being capable of moving in the aligned direction of the cartridges 104. The automatic nucleic acid extracting system 100 has recovering containers 106 and a rack 105 retaining the recovering containers 106. In a recovering step of recovering a nucleic acid that has been once adsorbed on an adsorbing medium provided in the cartridges 104 through a recovering solution, the recovering containers 106 recovers the recovering solution discharged from the cartridges 104.

In the automatic nucleic acid extracting system 100, after injecting a sample solution containing a nucleic acid or a solution, such as a rinsing solution and a recovering solution, into the cartridge 104 from an injecting nozzle, the pressure nozzle 101 is pressed onto an open end of the cartridge 104 to feed pressurized air to the interior of the cartridge 104 from the pressure nozzle, whereby the solution is passed through the adsorbing medium and discharged from the cartridge 104 to the recovering container 106 or a waste liquor container, which is not shown in the figure.

DISCLOSURE OF THE INVENTION

The nucleic acid extracting system 100 shown in FIG. 15 has such a constitution that upon injecting the recovering solution, the pressure nozzle 101 is pressed onto an air inlet opening of the cartridge 104 from above, and a cap, which is not shown in the figure, is mounted on the air inlet opening, so as to pressurize and seal the interior of the cartridge 104. In the constitution, there has been a demand of increasing the amount of the processed solution by increasing the area of the filter, and accordingly, it has been studied to use a cartridge 104 having a larger cross sectional area than the conventional one.

In the aforementioned conventional constitution, however, when the diameter of the cartridge 104 is increased for increasing the cross sectional area of the cartridge 104, the pressurizing force applied to the cap of the cartridge 104 upon pressurizing and sealing is also increased in proportion to the increase of the cross sectional area, and therefor it is necessary to change the structure of the apparatus to increase the strength thereof.

In the constitution shown in FIG. 16, in which upon extracting a nucleic acid from the filter F, a rubber pressure nozzle 101 is pressed onto the air inlet opening of the cartridge 104 to feed air thereinto, the pressure nozzle 101 receives a rising force $R=P \times S$ in the direction opposite to the pressing direction thereof, where P represents the pressure of the air, and S represents the cross sectional area of the cartridge 104.

In order to ensure airtightness of the interior of the cartridge 104, it is necessary that the pressing force A of the pressure nozzle 101 is larger than the rising force R, and thus the pressing force A is necessarily larger when the cross sectional area S of the cartridge 104 is increased. For example, in the case where the cross sectional area S is increased by 10 times, the force R applied to the pressure nozzle 101 is $P \times 10 \times S$, and thus the pressing force A should be increased by 10 times. In order to deal with the increased pressing force A only by the constitution of the apparatus, there is such a possibility that the pressing mechanism and the driving mechanism of the apparatus must be modified drastically.

Accordingly, there has been such a demand that a cartridge 104 having a larger diameter is used while maintaining airtightness of the cartridge, without drastic modification of the constitution of the apparatus.

The invention has been made under the circumstances, and an object thereof is to provide such a cartridge retaining mechanism for a nucleic acid extracting apparatus that can retain airtightness upon pressurizing, without drastic modification of the constitution of the nucleic acid extracting apparatus.

The aforementioned and other objects of the invention are attained by a cartridge retaining mechanism equipped in a nucleic acid extracting apparatus for extracting a nucleic acid, the cartridge retaining mechanism comprising a cartridge having a cylindrical shape with a bottom, having a nucleic acid-adsorbing solid carrier trapping a nucleic acid disposed at the bottom, and having the bottom being shaped in a funnel shape, and a cartridge retaining member retaining the cartridge, the cartridge retaining member having a supporting part supporting the cartridge and a pressure-proof retaining part attached to an open end of the cartridge, the pressure-proof retaining part having formed therein a nozzle receiving opening, onto which a pressure nozzle is pressed from a side of the nucleic acid extracting apparatus, and the cartridge being retained between the supporting part and the pressure-proof retaining part upon pressing the pressure nozzle onto the nozzle receiving opening.

According to the cartridge retaining mechanism having the aforementioned constitution according to the invention, the cartridge is supported by the supporting part of the cartridge retaining member and fixed by the pressure-proof retaining part thereof. The pressure-proof retaining part has, as an opening, the nozzle receiving opening, onto which the pressure nozzle is pressed from the side of the nucleic acid extracting apparatus. Upon extracting a nucleic acid by the nucleic acid extracting apparatus, the pressure nozzle is pressed onto the cartridge to feed pressurized air to the cartridge from the pressure nozzle, whereby the pressure directly applied to the pressure nozzle can be suppressed by the pressure-proof retaining part even though the internal pressure of the cartridge is increased, and airtightness of the interior of the cartridge can be ensured without release of the pressure nozzle from the nozzle receiving opening. In the constitution, accordingly, the increased pressure from the interior of the cartridge applied to the pressure nozzle upon increasing the diameter of the cartridge is received by the pressure-proof retaining part, whereby there is no necessity of modifying the mechanism of the nucleic acid extracting apparatus for pressing the pressure nozzle onto the cartridge.

In the cartridge retaining mechanism, it is preferred that the pressure-proof retaining part has equipped thereon a gasket part, with which the cartridge is in contact, upon pressing the pressure nozzle onto the nozzle receiving opening. According to the constitution, airtightness can be further ensured at the part where the gasket part of the pressure-proof retaining part and the cartridge are in contact with each other upon feeding pressurized air.

In the cartridge retaining mechanism, it is also preferred that the cartridge retaining mechanism further comprises an engaging member engaging the pressure-proof retaining part to the supporting part upon pressing the pressure nozzle onto the nozzle receiving opening. According to the constitution, the pressure-proof retaining part is engaged to supporting part with the engaging member upon pressurizing to fix the positions of them, and then the pressure nozzle is pressed onto the nozzle receiving opening for pressurizing. The cartridge can be taken out from the supporting part by releasing the engagement of the engaging member.

In the cartridge retaining mechanism, it is also preferred that the supporting part is equipped with a biasing member biasing the cartridge toward the pressure-proof retaining part. According to the constitution, the cartridge is pressed onto the retaining part with the biasing member upon feeding pressurized air, whereby the cartridge and the pressure-proof retaining part can be in contact with each other further firmly, and thus the pressurized air can be surely prevented from being leaked from the gap between them.

The aforementioned and other objects of the invention are attained by a cartridge retaining mechanism equipped in a nucleic acid extracting apparatus for extracting a nucleic acid, the cartridge retaining mechanism comprising a cartridge having a cylindrical shape with a bottom, having a nucleic acid-adsorbing solid carrier trapping a nucleic acid disposed at the bottom, and having the bottom being shaped in a funnel shape, a cartridge retaining member retaining the cartridge, and a cap detachably mounted on an open end of the cartridge, the cartridge retaining member having a supporting part supporting the cartridge and a pressure-proof retaining part holding the cap, the pressure-proof retaining part having formed therein an opening, through which a pressure nozzle is inserted from a side of the nucleic acid extracting apparatus, the cap having formed therein a nozzle receiving opening, onto which the pressure nozzle is pressed, the nozzle receiving opening being connected to the opening, and the cartridge being retained between the supporting part and the pressure-proof retaining part upon pressing the pressure nozzle onto the nozzle receiving opening.

According to the cartridge retaining mechanism having the aforementioned constitution according to the invention, the cartridge is supported by the supporting part of the cartridge retaining member and fixed by the pressure-proof retaining part thereof. The cartridge is equipped with the cap. The pressure nozzle on the side of the nucleic acid extracting apparatus is inserted through the opening of the supporting part, and the pressure nozzle is pressed onto the nozzle receiving opening of the cap. Upon extracting a nucleic acid by the nucleic acid extracting apparatus, the pressure nozzle is pressed onto the cartridge to feed pressurized air to the cartridge from the pressure nozzle, whereby even though the internal pressure of the cartridge is increased, the cap pressed onto the pressure-proof retaining part suppresses the pressure applied from the cartridge to lower the pressure directly applied to the pressure nozzle, and thus a gap between the pressure nozzle and the nozzle receiving opening of the cap can be prevented from occurring. Consequently, airtightness of the interior of the cartridge can be ensured without leakage of pressurized air. In the constitution, accordingly, the increased pressure from the interior of the cartridge applied to the pressure nozzle upon increasing the diameter of the cartridge is received by the fixed pressure-proof retaining part through the cap, whereby there is no necessity of modifying the mechanism of the nucleic acid extracting apparatus for pressing the pressure nozzle onto the cartridge.

In the cartridge retaining mechanism, it is preferred that the cap has formed thereon a fitting part fitting with the cartridge, and the fitting part is equipped with a sealing member contacting with the cartridge.

In view of above, the invention provides the followings, but is not limited thereto.

(1) A cartridge retaining mechanism equipped in a nucleic acid extracting apparatus for extracting a nucleic acid, the cartridge retaining mechanism comprising:

a cartridge having a cylindrical shape with a bottom, and the bottom is shaped in a funnel shape;

a nucleic acid-adsorbing solid carrier that traps a nucleic acid, and the nucleic acid-adsorbing solid carrier is disposed at the bottom of the cartridge; and a cartridge retaining member that retains the cartridge, wherein the cartridge retaining member comprises: a supporting part that supports the cartridge; and a pressure-proof retaining part that is attached to an open end of the cartridge, and wherein the pressure-proof retaining part has a nozzle receiving opening, onto which a pressure nozzle of the nucleic acid extracting apparatus is pressed, and wherein the cartridge is retained between the supporting part and the pressure-proof retaining part upon pressing the pressure nozzle onto the nozzle receiving opening.

(2) The cartridge retaining mechanism as described in (1) above, wherein the pressure-proof retaining part comprises a gasket part, which is in contact with the cartridge upon pressing the pressure nozzle onto the nozzle receiving opening.

(3) The cartridge retaining mechanism as described in (1) or (2) above, wherein the cartridge retaining mechanism further comprises an engaging member that engages the pressure-proof retaining part to the supporting part upon pressing the pressure nozzle onto the nozzle receiving opening.

(4) The cartridge retaining mechanism as described in any of (1) to (3) above, wherein the supporting part comprises a biasing member that biases the cartridge toward the pressure-proof retaining part.

(5) A cartridge retaining mechanism equipped in a nucleic acid extracting apparatus for extracting a nucleic acid, the cartridge retaining mechanism comprising:

a cartridge having a cylindrical shape with a bottom, and the bottom is shaped in a funnel shape;

a nucleic acid-adsorbing solid carrier that traps a nucleic acid, and the nucleic acid-adsorbing solid carrier is disposed at the bottom of the cartridge;

a cartridge retaining member that retains the cartridge; and a cap that is detachably mounted on an open end of the cartridge, wherein the cartridge retaining member comprises: a supporting part that supports the cartridge; and a pressure-proof retaining part that holds the cap, and wherein the pressure-proof retaining part has an opening, through which a pressure nozzle of the nucleic acid extracting apparatus is inserted, and the cap has a nozzle receiving opening, onto which the pressure nozzle is pressed, and the nozzle receiving opening is connected to the opening of the pressure-proof retaining part, and wherein the cartridge is retained between the supporting part and the pressure-proof retaining part upon pressing the pressure nozzle onto the nozzle receiving opening.

(6) The cartridge retaining mechanism as described in (5) above, wherein the cap has a fitting part that fits with the cartridge, and the cap comprises a sealing member, which is in contact with the cartridge and equipped in the fitting part.

BEST MODE FOR CARRYING OUT THE INVENTION

Embodiments of the invention will be described below with reference to the drawings.

Figure 1:
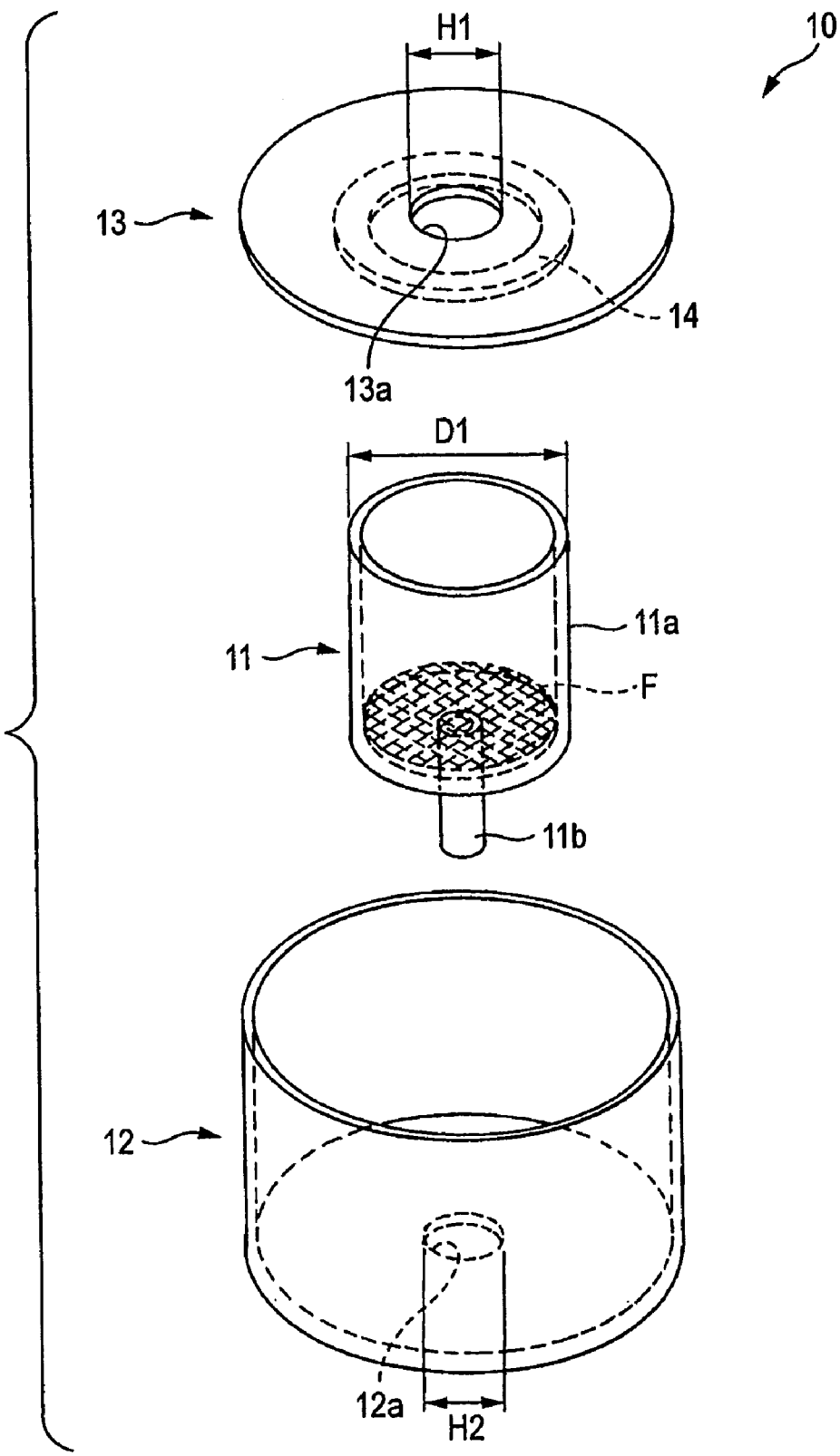
FIG. 1 is an exploded perspective view showing a first embodiment of a cartridge retaining mechanism according to the invention.
Figure 2:
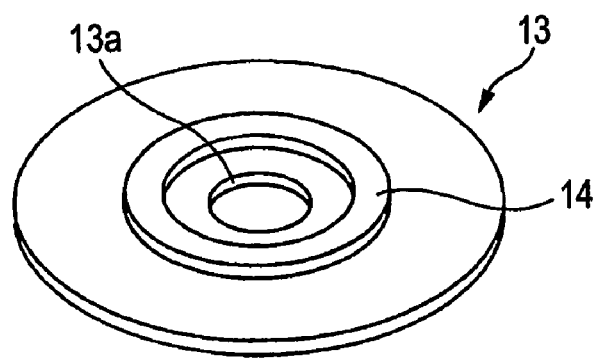
FIG. 2 is a perspective view showing a pressure-proof retaining part of the first embodiment shown in FIG. 1.
Figure 3:
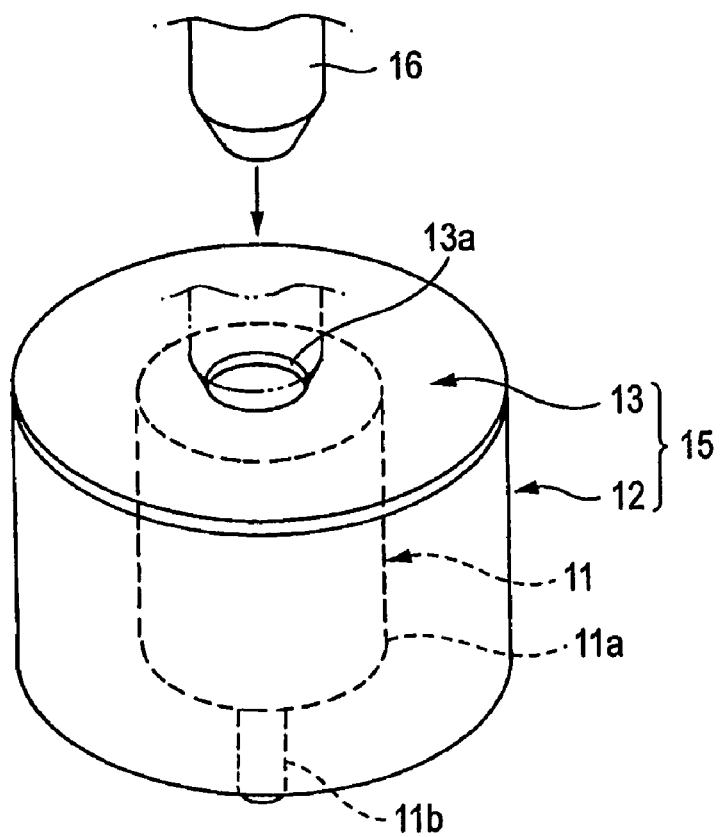
FIG. 3 is an illustrative diagram showing the state where a pressure nozzle is being pressed onto a cartridge retaining member.
Figure 4:
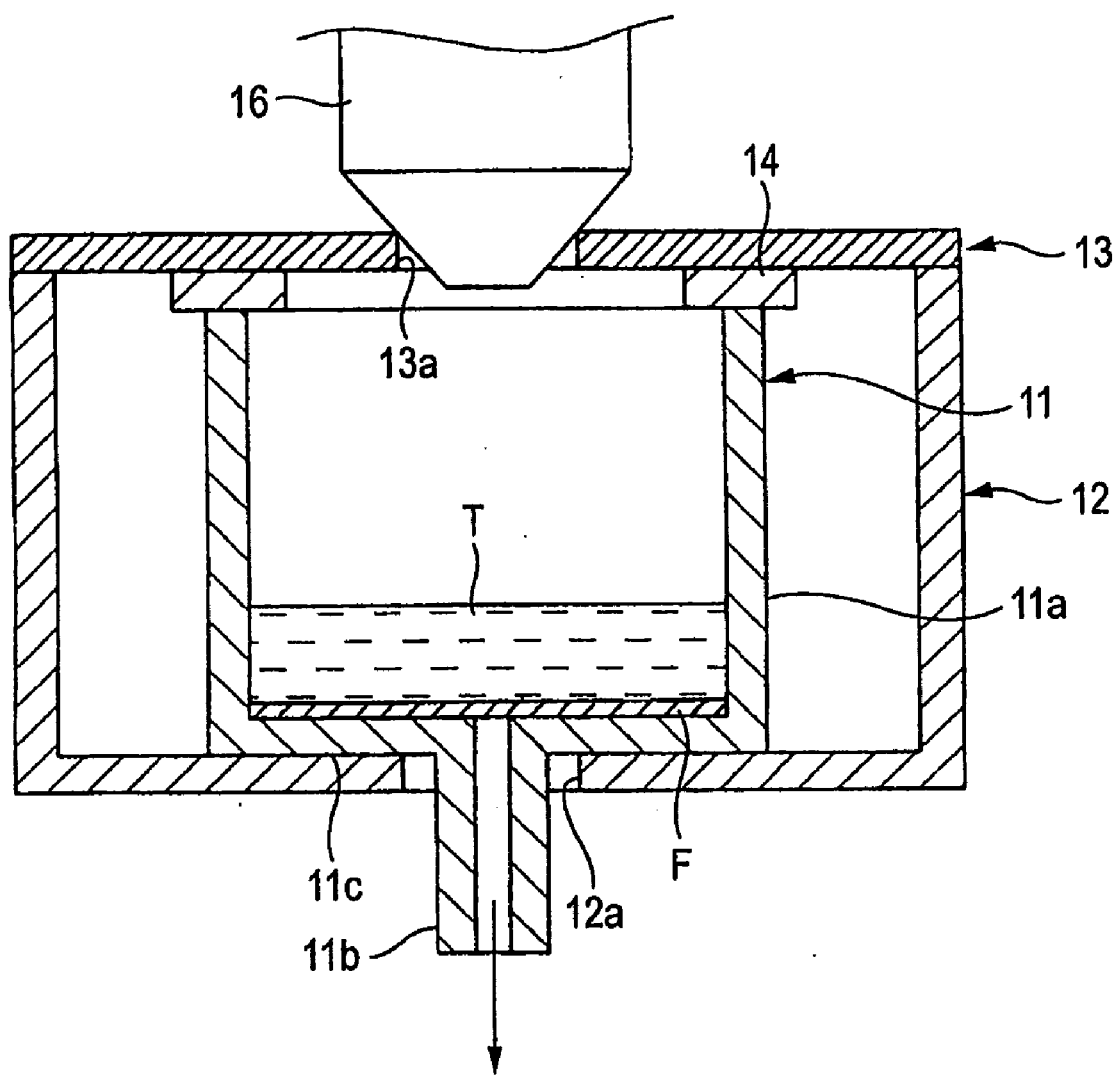
FIG. 4 is a cross sectional view showing the state where the pressure nozzle is pressed onto the cartridge retaining member.

FIG. 1 is an exploded perspective view showing a first embodiment of the cartridge retaining mechanism according to the invention. FIG. 2 is a perspective view showing a pressure-proof retaining part of the first embodiment shown in FIG. 1. FIG. 3 is an illustrative diagram showing the state where a pressure nozzle is being pressed onto a cartridge retaining member. FIG. 4 is a cross sectional view showing the state where the pressure nozzle is pressed onto the cartridge retaining member.

The cartridge retaining member of the invention is equipped in a nucleic acid extracting apparatus. The nucleic acid extracting apparatus carries out the following step in this order, i.e., (1) a step of passing a sample solution containing a nucleic acid through a nucleic acid-adsorbing porous membrane disposed in a cartridge to adsorb the nucleic 15 acid in the nucleic acid-adsorbing porous membrane, (2) a step of rinsing the nucleic acid-adsorbing membrane having the nucleic acid adsorbed therein, (3) a step of passing a recovering solution through the nucleic acid-adsorbing porous membrane to release the nucleic acid from the nucleic acid-adsorbing membrane and to recover the nucleic acid.

The sample solution, the rinsing solution and the recovering solution (which will be generically referred to as a solution) are injected into the cartridge with an injecting nozzle, and then pressurized air is fed into the cartridge with a pressure nozzle, whereby the solution is discharged from the cartridge to a recovering container or the like. The cartridge retaining mechanism has such a function that it retains the cartridge upon feeding pressurized air from the pressure nozzle to the cartridge.

As shown in FIG. 1, the cartridge retaining mechanism 10 retains a cartridge 11 having a cylindrical shape with a bottom, in which an opening is formed on the upper side, and a bottom having a funnel shape is formed on the lower side. The cartridge 11 has a cylindrical body 11a and a discharging part 11b having a thin tube nozzle shape extending from the center of the end surface of the bottom to the exterior. In this embodiment, the body 11a has a diameter D1 of from 5 to 30 mm.

A nucleic acid-adsorbing porous membrane F is retained at the bottom of the cylindrical body 11a of the cartridge 11. The nucleic acid-adsorbing porous membrane F will be described later in detail.

The cartridge retaining mechanism 10 has a supporting part 12 in a container form, in which the cartridge 11 is installed, and a pressure-proof retaining part 13, which is mounted over the supporting part 12 and retains the cartridge 11 installed in the supporting part 12.

The supporting part 12 is a member having a container form with a diameter larger than the diameter D1 of the cartridge. The supporting part 12 has an upper opening at the upper end opened upward. A through hole 12a, through which the discharging part 11b of the cartridge is inserted, is formed at the center of the bottom of the supporting part 12. The opening diameter H2 of the through hole 12a is slightly larger than the diameter of the discharging part 11b.

The pressure-proof retaining part 13 is a member having a substantially disk shape capable of plugging the upper opening of the supporting part 12 upon mounting on the upper opening, and has formed at the center thereof a nozzle receiving opening 13a, onto which a pressure nozzle 16 is pressed from the side of the nucleic acid extracting apparatus. The nozzle receiving opening 13a has an opening diameter H1 that is slightly larger than the diameter of the nozzle tip of the pressure nozzle 16 for fitting the nozzle tip thereto.

As shown in FIGS. 1 and 2, a gasket part 14 in a ring form is provided on the surface of the pressure-proof retaining part 13 on the side of the cartridge 11 in such a manner that upon mounting the pressure-proof retaining part 13 on the supporting part 12, the gasket part 14 is in contact with the upper periphery of the cartridge 11. The gasket part 14 is formed, for example, with a resin material, such as a silicone resin, to have a thickness of from 1 to 5 mm. The gasket part 14 is close contact with the cartridge 11 installed in the supporting part 12 upon pressing the pressure nozzle 16 onto the nozzle receiving opening 13a, whereby airtightness can be further certainly ensured at the part where the gasket part 14 of the pressure-proof retaining part 13 is in contact with the cartridge 11.

As shown in FIGS. 3 and 4, for installing the cartridge 11 in the supporting part 12, the cartridge 11 is inserted from the upper opening of the supporting part 12, and the discharging part 11b is inserted into the through hole 12a of the supporting part 12 with a lower surface 11c of the cylindrical body 11a being in contact with the upper surface of the bottom of the supporting part 12.

The supporting part 12 and the pressure-proof retaining part 13 constitute a cartridge retaining member 15. The cartridge retaining member 15 houses the cartridge 11 in the supporting part 12 and retains the cartridge 11 between the supporting part 12 and the pressure-proof retaining part 13 under the state where the pressure-proof retaining part 13 is fixed on the supporting part 12 to plug the upper opening thereof, and the pressure nozzle 16 is pressed onto the nozzle receiving opening 13a.

Upon feeding pressurized air, the supporting part 12 and the pressure-proof retaining part 13 of the cartridge retaining member 15 are combined and fixed with each other to ensure airtightness of the cartridge 11.

In the case where pressurized air is to be fed to the cartridge having a solution T having been injected therein upon extracting a nucleic acid, the pressure nozzle 16 is pressed onto the nozzle receiving opening 13a of the pressure-proof retaining part 13 in the state where the cartridge 11 is retained in the cartridge retaining member 15. Upon feeding pressurized air from the pressure nozzle 16 to the interior of the cartridge 11, the interior of the cartridge 11 is pressurized, and the solution T is discharged from the discharging part 11b through the nucleic acid-adsorbing porous membrane.

In the cartridge retaining mechanism 10 of this embodiment, the cartridge 11 is supported by the supporting part 12 of the cartridge retaining member 15 and fixed by the pressure-proof retaining part 13. The pressure-proof retaining part 13 has, as an opening, the nozzle receiving opening 13a, onto which the pressure nozzle 16 is pressed from the side of the nucleic acid extracting apparatus. Upon extracting a nucleic acid by the nucleic acid extracting apparatus, the pressure nozzle 16 is pressed onto the cartridge 11 to feed pressurized air to the cartridge 11 from the pressure nozzle 16, whereby the pressure directly applied to the pressure nozzle 16 can be suppressed by the pressure-proof retaining part 13 even though the internal pressure of the cartridge 11 is increased, and airtightness of the interior of the cartridge 11 can be ensured without release of the pressure nozzle 16 from the nozzle receiving opening 13a. In the embodiment, accordingly, the increased pressure from the interior of the cartridge 11 applied to the pressure nozzle 16 upon increasing the diameter of the cartridge 11 is received by the pressure-proof retaining part 13, whereby there is no necessity of modifying the mechanism of the nucleic acid extracting apparatus for pressing the pressure nozzle 16 onto the cartridge 11.

A second embodiment of the cartridge retaining mechanism according to the invention will be described with reference to FIGS. 5 and 6. In the following description of the embodiment, members having the constitutions and functions that are equivalent to the members having been described are attached with the same symbols or the corresponding symbols to simplify or omit the detailed descriptions thereof.

Figure 5:
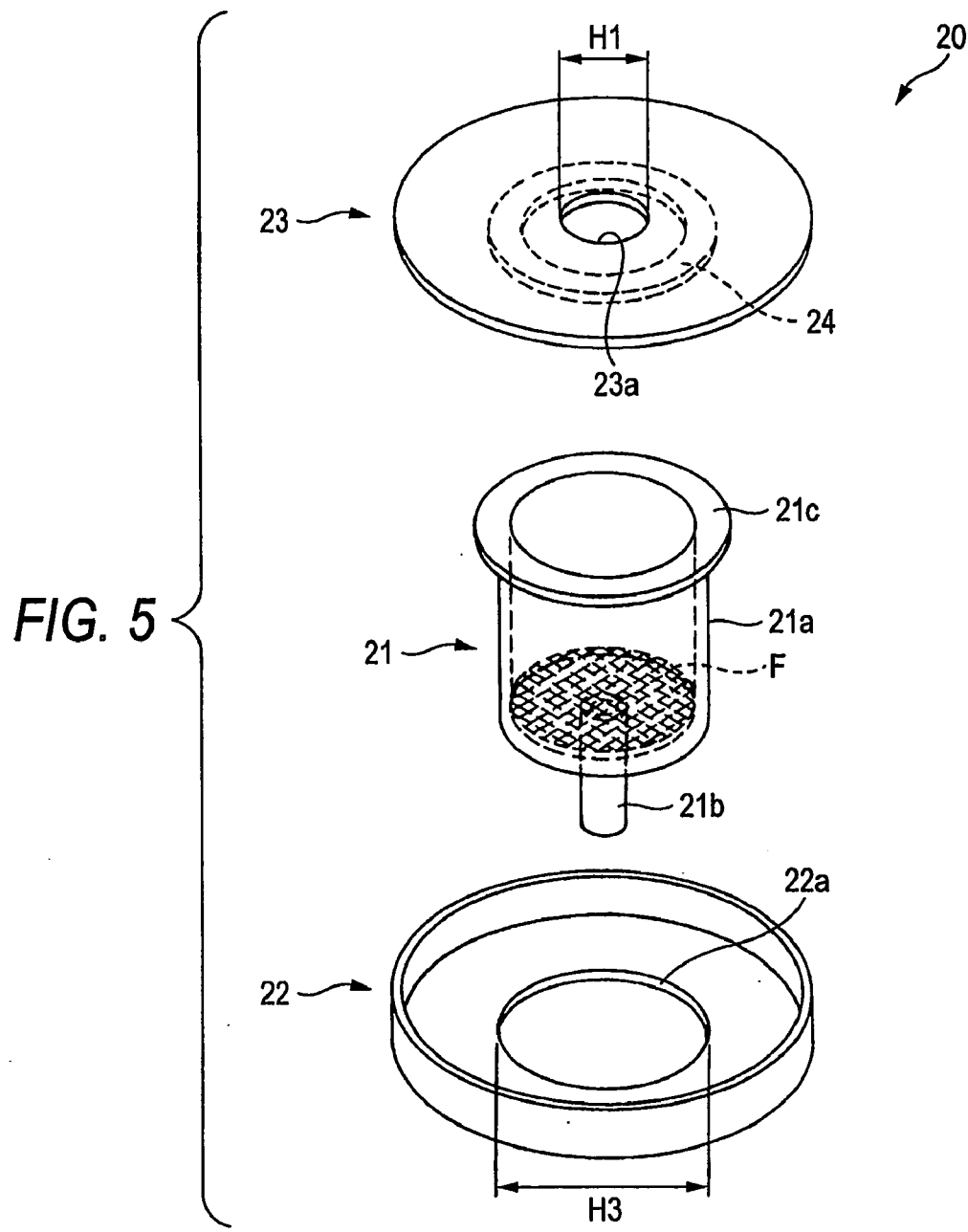
FIG. 5 is an exploded perspective view showing a second embodiment of a cartridge retaining mechanism according to the invention.

FIG. 5 is an exploded perspective view showing the second embodiment of the cartridge retaining mechanism according to the invention. FIG. 6 is a cross sectional view showing the cartridge retaining mechanism in the state where the pressure nozzle is pressed thereon.

Figure 6:
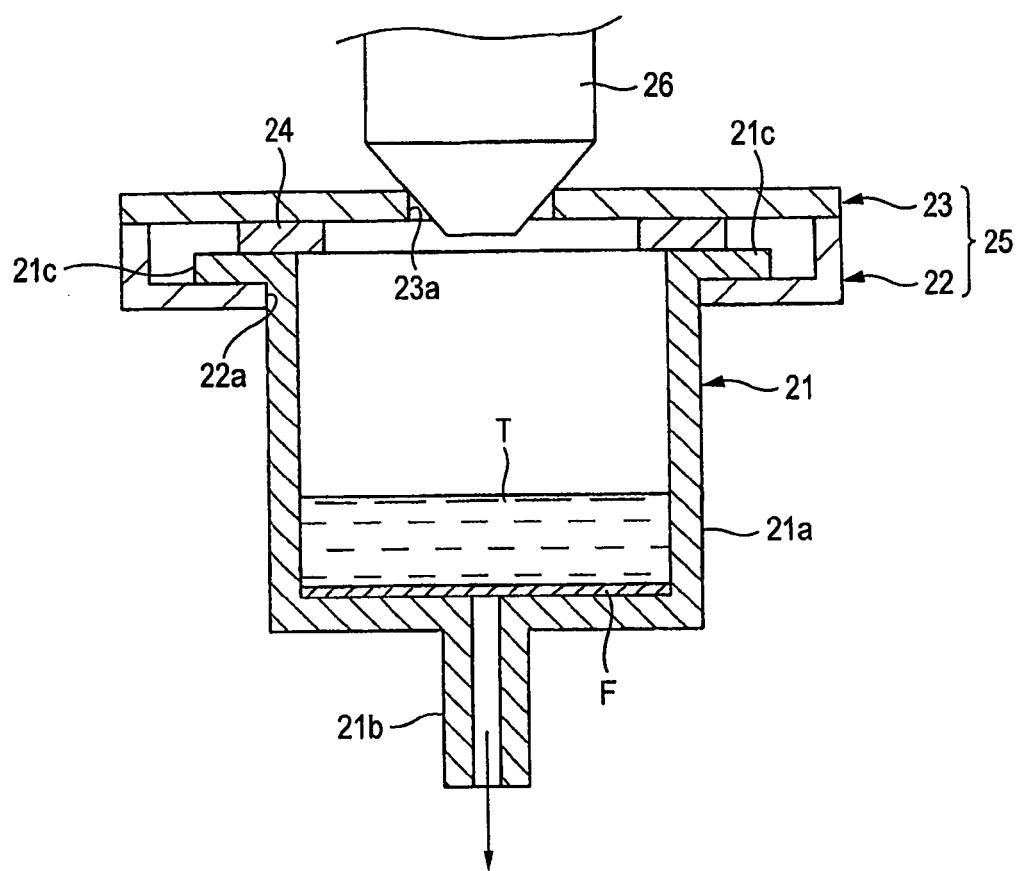
FIG. 6 is a cross sectional view showing the cartridge retaining mechanism in the state where a pressure nozzle is pressed thereon.

As shown in FIGS. 5 and 6, the cartridge retaining mechanism 20 of the embodiment has a cartridge 21 and a cartridge retaining member 25 housing and retaining the cartridge 21. The cartridge retaining member 25 is constituted by a supporting part 22 and a pressure-proof retaining part 23.

As shown in FIG. 5, the cartridge 21 has a flange part 21c extending outward in the diameter direction from an open end of a cylindrical body 21a of the cartridge 21. A through hole 22a, through which the cylindrical body 21a of the cartridge 21 is inserted, is formed at the center of the bottom of the supporting part 22. The opening diameter H3 of the through hole 22a is slightly larger than the diameter of the cylindrical body 21a.

In the cartridge retaining mechanism 20 of the embodiment, the cartridge 21 is inserted in the through hole 22a to make the flange part 21c in contact with the upper surface of the bottom of the supporting part 22, and the pressure-proof retaining part 23 is mounted on the upper opening of the supporting part 22. The pressure-proof retaining part 23 has, on the surface thereof on the side of the cartridge 22, a gasket part 24 in a ring form as similar to the first embodiment, and the gasket part 24 is in contact with the upper part of the flange part 21c of the cartridge 21 housed and supported in the supporting part 22.

As shown in FIG. 6, the pressure-proof retaining part 23 is mounted on the supporting part 22 to hold the flange part 21c of the cartridge 21 between the gasket part 24 of the pressure-proof retaining part 23 and the supporting part, whereby the cartridge 21 is retained with airtightness ensured. The cartridge retaining member 25 in this state is fixed to the nucleic acid extracting apparatus.

Upon feeding pressurized air to the cartridge, a pressure nozzle 26 is pressed onto a nozzle receiving opening 23a of the pressure-proof retaining part 23 in the state where the cartridge 21 is retained in the cartridge retaining member 25. Upon feeding pressurized air from the pressure nozzle 26 to the interior of the cartridge 21, the interior of the cartridge 21 is pressurized, and a solution T is discharged from a discharging part 21b through the nucleic acid-adsorbing porous membrane. At this time, airtightness of the cartridge 21 is ensured by the cartridge retaining member 25, and therefore, even though the diameter of the cartridge 21 is increased, the pressure from the interior of the cartridge 21 applied to the pressure nozzle 26 is received by the fixed pressure-proof retaining part 23, whereby there is no necessity of modifying the mechanism of the nucleic acid extracting apparatus for pressing the pressure nozzle 26.

Figure 7:
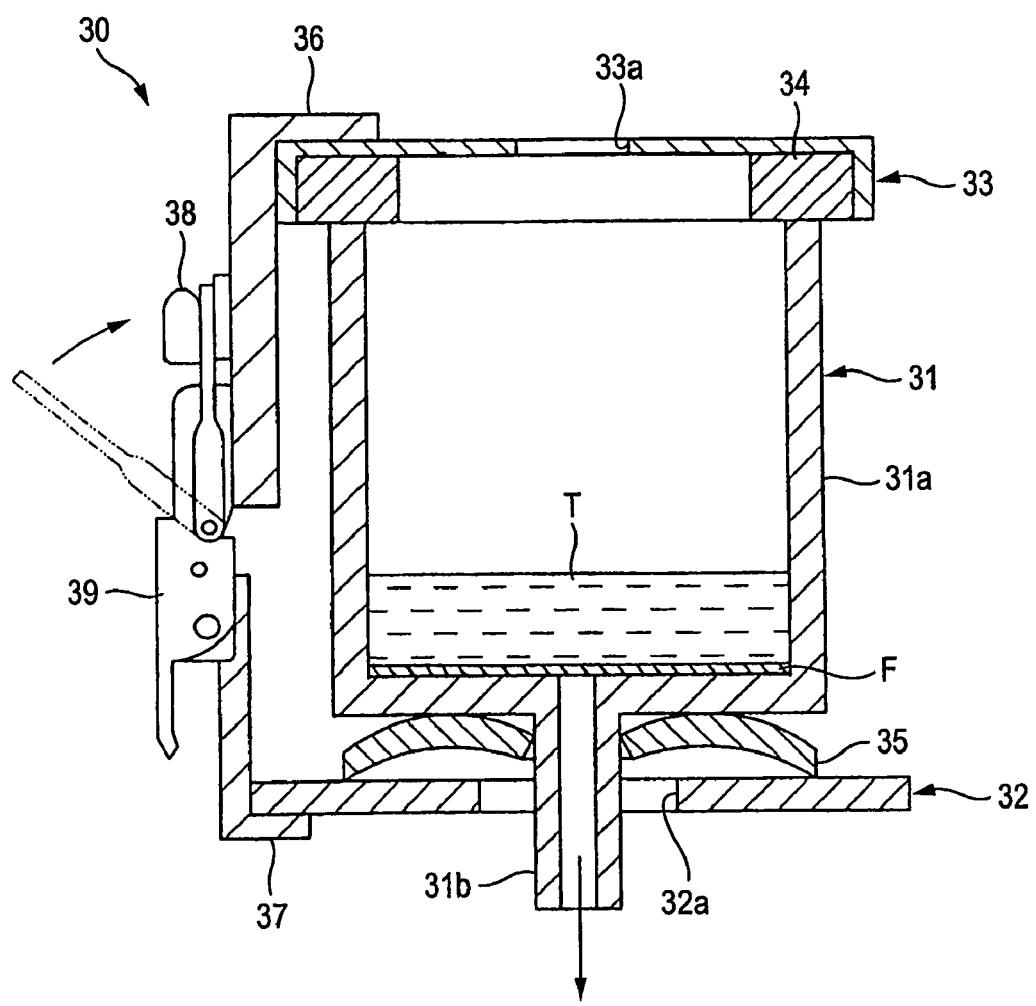
FIG. 7 is a cross sectional view showing a third embodiment of a cartridge retaining mechanism according to the invention.

FIG. 7 is a cross sectional view showing a third embodiment of the cartridge retaining mechanism according to the invention. The cartridge retaining mechanism 30 has a supporting part 32, in which a cartridge 31 is installed, and a pressure-proof retaining part 33 in a lid form mounted on an upper part of the supporting part 32, and the supporting part 32 and the pressure-proof retaining part 33 constitute a cartridge retaining member.

The pressure-proof retaining part 33 has, on a lower surface thereof, a gasket part 34 in a ring form, which is in contact with an upper periphery of a cylindrical body 31a of the cartridge 31. The pressure-proof retaining part 33 has formed therein a nozzle receiving opening 33a, onto which a pressure nozzle of the nucleic acid extracting apparatus is pressed.

The supporting part 32 has formed therein a through hole 32a, through which a discharging part 31b of the installed cartridge 31 is inserted. A biasing member 35, such as a wave washer and a backup spring, is provided between the lower end surface of the cylindrical body 31a of the cartridge 31 and the upper surface of the supporting part 32.

A first supporting member 36 having a substantially L-cross sectional shape is fixed over the upper end to the periphery of the pressure-proof retaining part 33, and a second supporting member 37 having a substantially L-cross sectional shape is fixed over the lower end to the periphery thereof. The first supporting member 36 has an engaging projection 38, and the second supporting member 37 has an engagement driving member 39. The engagement driving member 39 is engaged with the engaging projection 38, whereby the pressure-proof retaining part 33 having the first supporting member 36 fixed thereto and the supporting part 32 having the second supporting member fixed thereto can be fixed to each other. The engaging projection 38 and the engagement driving member 39 function as an engaging member in pairs. The constitution of the engaging member is not limited to the aforementioned pair of the engaging projection 38 and the engagement driving member 39, and other constitutions may be employed.

In the cartridge retaining mechanism 30 of the embodiment, the discharging part 31b of the cartridge 31 is inserted in the through hole 32a, the lower end of the cartridge 31 is supported by the upper surface of the supporting part 32 through the biasing member 35, and the a gasket part 34 is pressed onto the upper periphery of the cartridge 31. The engagement driving member 39 is engaged with the engaging projection 38 to fix the supporting part 32 and the pressure-proof retaining part 33 to each other. According to the constitution, even when pressurized air is fed to the cartridge 31 by pressing the pressure nozzle onto the nozzle receiving opening 33a of the pressure-proof retaining part 33 to pressurize the interior of the cartridge 31, the pressure-proof retaining part 33 can be prevented from being released from the cartridge 31 under pressure from the cartridge 31 because the pressure-proof retaining part 33 is fixed to the supporting part 32.

In the cartridge retaining mechanism 30 of the embodiment, the cartridge 31 is pressed onto the side of the pressure-proof retaining part 33 with the biasing member 35, whereby the cartridge 31 and the pressure-proof retaining member 33 can be made in firmly contact with each other, and thus pressurized air can be further surely prevented from being leaked from the gap between them.

The pressure-proof retaining part 33 has the gasket part 34, which is pressed onto the cartridge 31, whereby upon feeding pressurized air, airtightness at the part where the gasket part 34 of the pressure-proof retaining part 33 and the cartridge 31 are in contact with each other can be further ensured.

Figure 8:
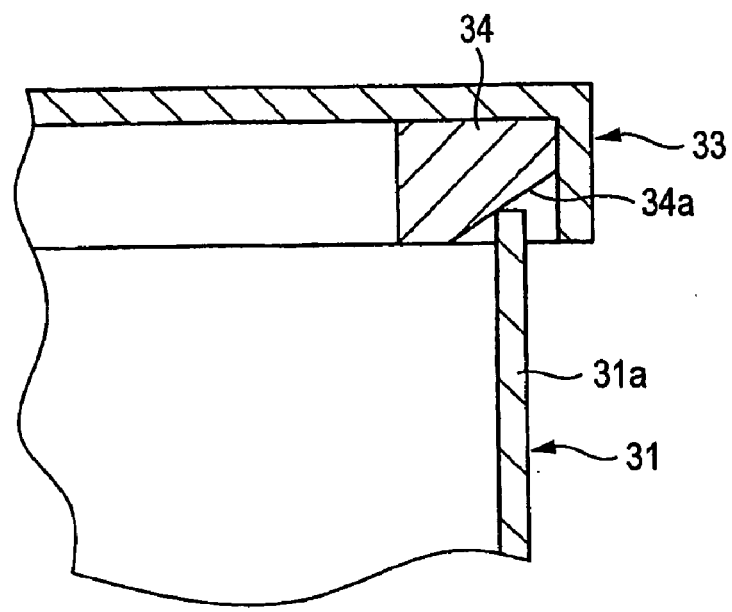
FIG. 8 is a partial cross sectional view showing an example where a taper surface is formed on an outside of a gasket part in a ring form.
Figure 9:
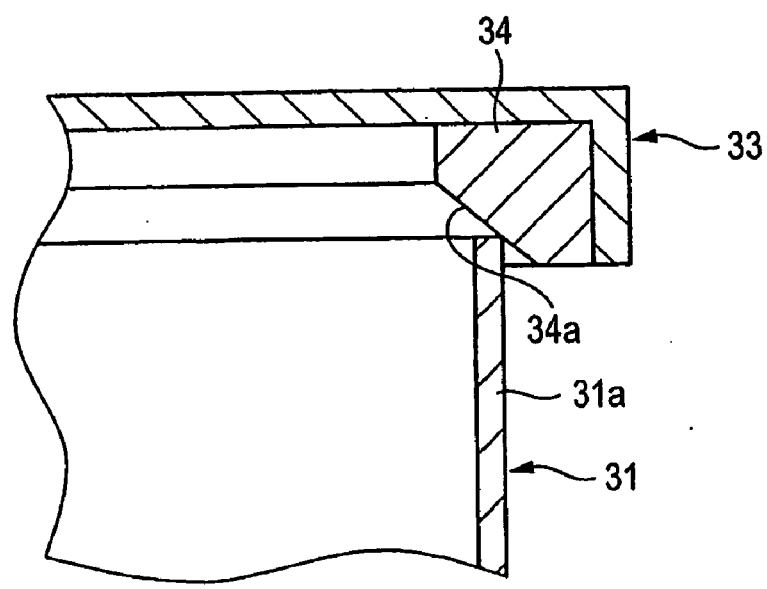
FIG. 9 is a partial cross sectional view showing an example where a taper surface is formed on an inside of a gasket part in a ring form.

The adhesion force of the gasket part 34 in a ring form to the cartridge 31 can be improved by forming a taper surface on an inside or outside of the gasket part 34. FIG. 8 is a partial cross sectional view showing an example where a taper surface is formed on an outside of the gasket part in a ring form. FIG. 9 is a partial cross sectional view showing an example where a taper surface is formed on an inside of the gasket part in a ring form.

As shown in FIG. 8, the gasket part 34 in a ring form has formed thereon a taper surface 34a inclining toward the outside. In this case, upon pressing the pressure-proof retaining part 33 onto the upper periphery of the cartridge 31, a stress occurs on a side wall of the cylindrical body 31 in the diameter direction to improve the adhesion force between the gasket part 34 and the cartridge 31.

As shown in FIG. 9, the gasket part 34 in a ring form has formed thereon a taper surface 34a inclining toward the inside as similar to the aforementioned case. In this case, upon pressing the pressure-proof retaining part 33 onto the upper periphery of the cartridge 31, a stress occurs on a side wall of the cylindrical body 31 in the diameter direction to improve the adhesion force between the gasket part 34 and the cartridge 31.

A fourth embodiment of the cartridge retaining mechanism according to the invention will be described.

Figure 10:
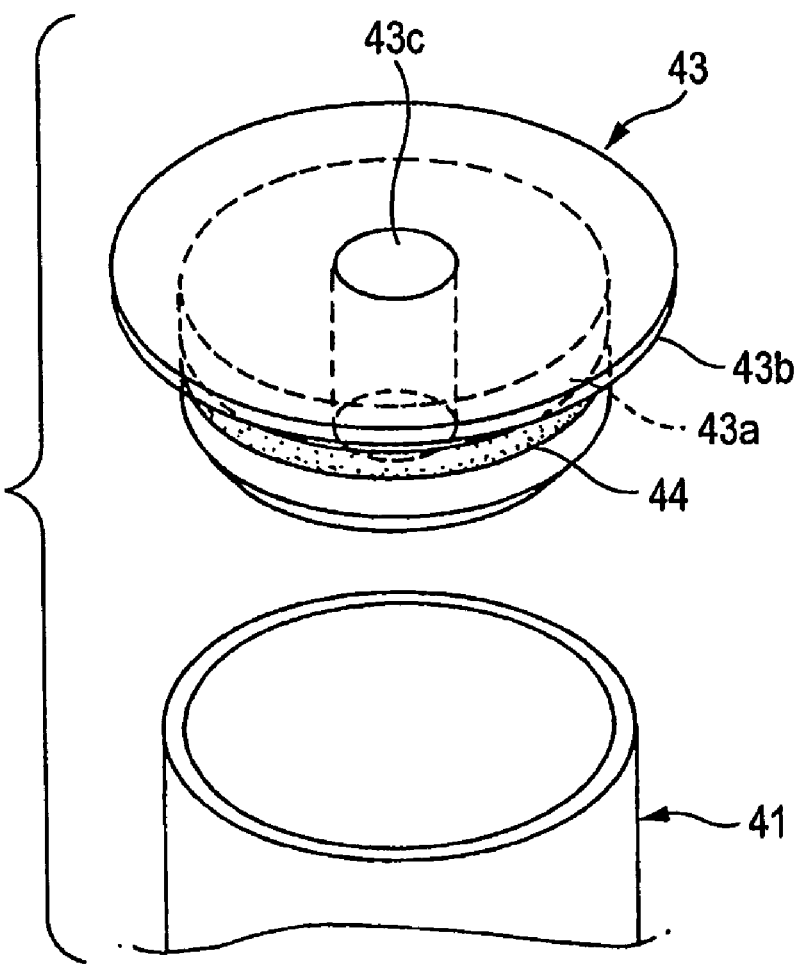
FIG. 10 is a perspective view showing a cap mounted on a cartridge.
Figure 11:
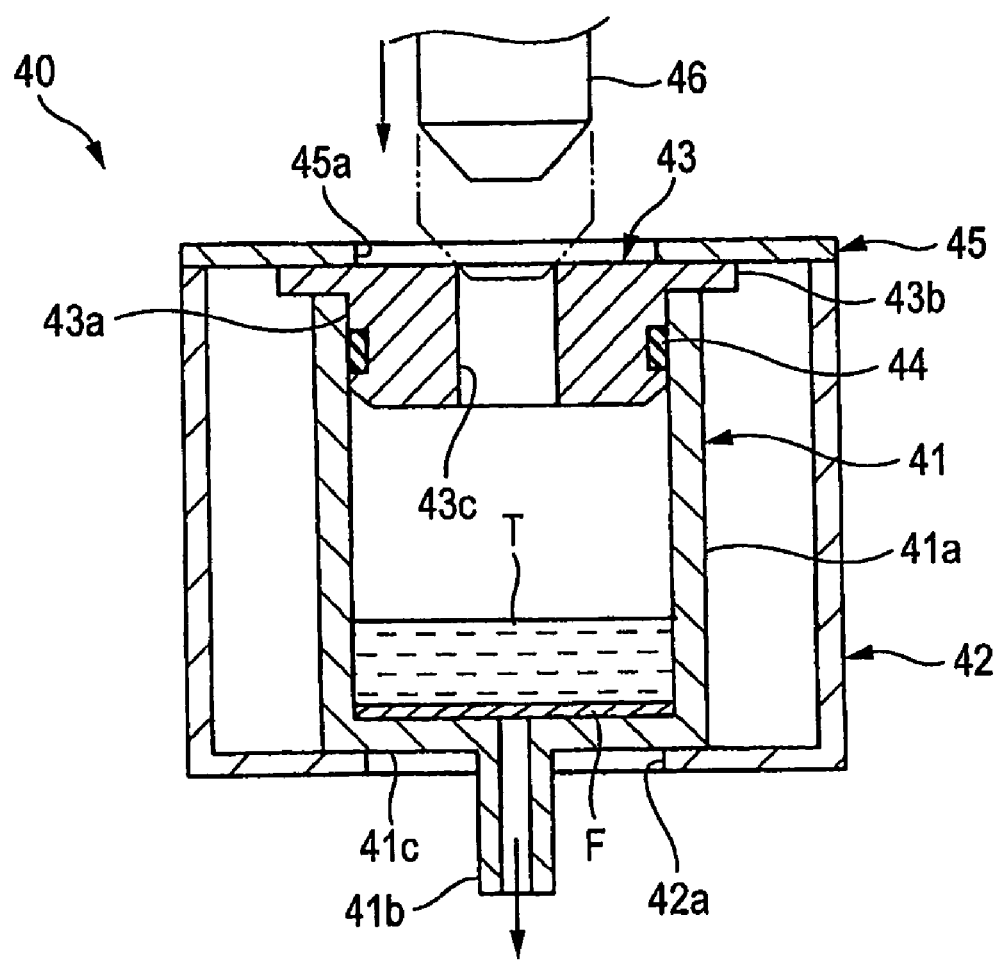
FIG. 11 is a cross sectional view showing a cartridge retaining mechanism of a fourth embodiment.

FIG. 10 is a perspective view showing a cap mounted on a cartridge. FIG. 11 is a cross sectional view showing the cartridge retaining mechanism of the embodiment.

The cartridge retaining mechanism 40 has the same constitution as the aforementioned embodiments in a point that it has a cartridge 41, and for housing and retaining the cartridge 41 a supporting part 42 in a container form and a pressure-proof retaining part 45 mounted on an open end of the supporting part 42. However, the fourth embodiment is different from the other embodiments in such a way that a cap 43 is detachably mounted on the open end of the cartridge 41.

As shown in FIG. 10, the cap 43 has a fitting part 43a in a cylindrical form, a locking part 43b projected from an upper end of the fitting part 43a in the diameter direction, and a nozzle receiving opening 43c penetrating the fitting part 43a in the axial direction.

A sealing member 44 in a ring form is fitted on a peripheral surface of the fitting part 43a. Examples of the sealing member 44 include a gasket and an O-ring. The fitting part 43 a is fitted to the open end of the cartridge 41, whereby the gap between the cartridge 41 and the cap 43 is sealed with the sealing member 44 to prevent pressurized air from being leaked from the cartridge 41.

The pressure-proof retaining part 45 has an opening 45a connected to the nozzle receiving opening 43c of the cap 43. The opening 45a has a sufficiently larger open diameter than the nozzle receiving opening 43c for preventing the pressure-proof retaining part 45 from interfering a pressure nozzle 46 pressed onto the nozzle receiving opening 43c of the cap 43.

Upon feeding pressurized air, the cap 43 is mounted on the open end of the cartridge 41, and the cartridge is installed in the supporting part 42 to insert the discharging part 41b through the through hole 42a of the supporting part 42. The pressure-proof retaining part 45 is made in contact with the upper surface of the locking part 43b of the cap 43 and mounted on the supporting part 42, and the pressure nozzle 46 is inserted in the opening 45a and pressed onto the nozzle receiving opening 43c of the cap 43. When the pressure in the cartridge 41 is increased by feeding pressurized air from the pressure nozzle 46 to the cartridge 41 for discharging a solution T having been injected therein, the open end of the cartridge 41 is sealed with the cap 43 and the pressure-proof retaining part 45 pressing the cap 43. According to the constitution, pressurized air fed to the cartridge 41 can be prevented from being leaked to ensure airtightness, and thus the solution T is discharged from the discharging part 41b through the nucleic acid-adsorbing porous membrane F.

Figure 12:
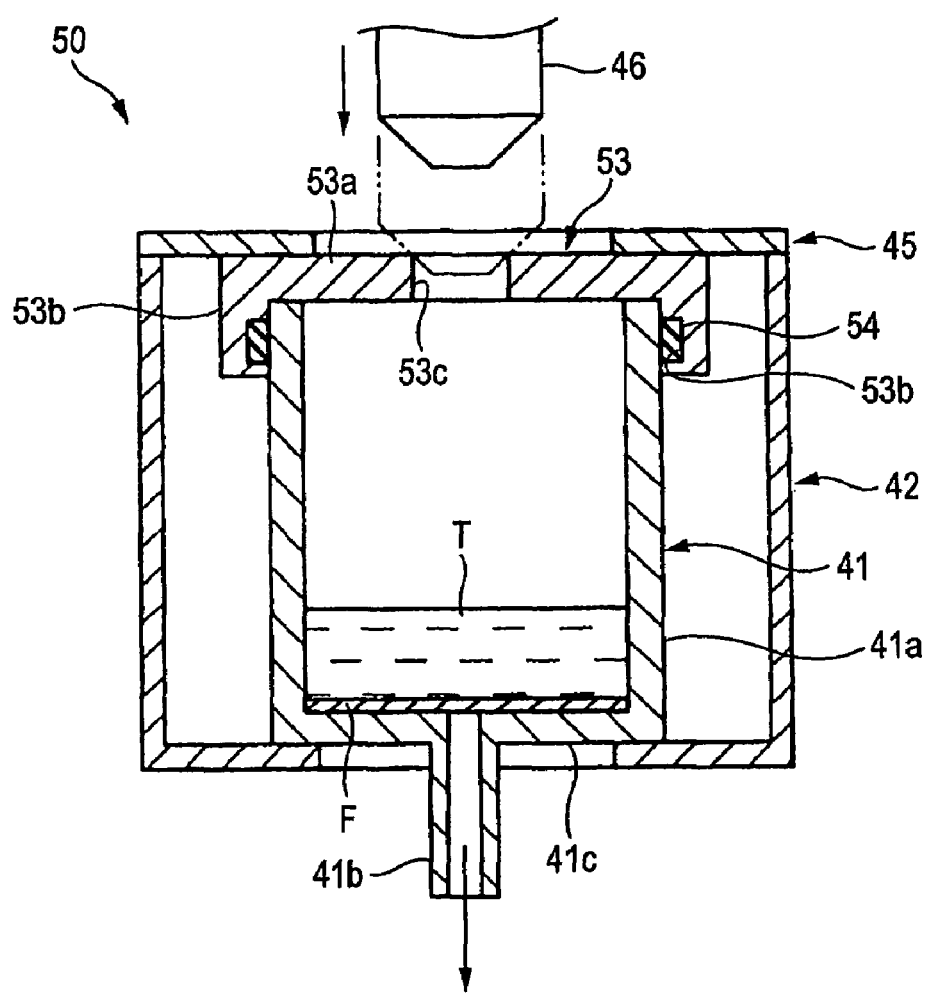
FIG. 12 is a cross sectional view showing a fifth embodiment of a cartridge retaining mechanism according to the invention.

FIG. 12 is a cross sectional view showing a fifth embodiment of the cartridge retaining mechanism according to the invention.

The cartridge retaining mechanism 50 of the embodiment has basically the same constitution as in the fourth embodiment, and has only the following differences.

As shown in FIG. 12, a cap 53 of the cartridge retaining mechanism 50 is fitted to an outer periphery of an open end of a cylindrical body 41a of a cartridge 41, and the cap 53 has a top panel 53a in a disk form closing the open end and a fitting part 53b in a ring form set up from the periphery of the top panel 53a.

A sealing member 54 in a ring form is fitted onto an inner surface of the fitting part 53b. As the sealing member 54, those having the same shapes and formed of the same materials as the sealing member 44 of the fourth embodiment may be used. Upon fitting the fitting part 53b of the cap 53 to the open end of the cartridge 41, the gap between the cartridge 41 and the cap 53 is sealed with the sealing member 54 to prevent pressurized air from being leaked from the cartridge 41.

According to the cartridge retaining mechanism 50 of the embodiment, even though the pressure inside the cartridge 41 is increased upon feeding pressurized air thereto, the open end of the cartridge 41 is sealed with the cap 53 and the pressure-proof retaining part 45 retaining the cap 53. According to the constitution, pressurized air fed to the cartridge 41 is prevented from being leaked to ensure air tightness, and thus the solution T is discharged from the discharging part 41b through the nucleic acid-adsorbing porous membrane F.

Figure 13:
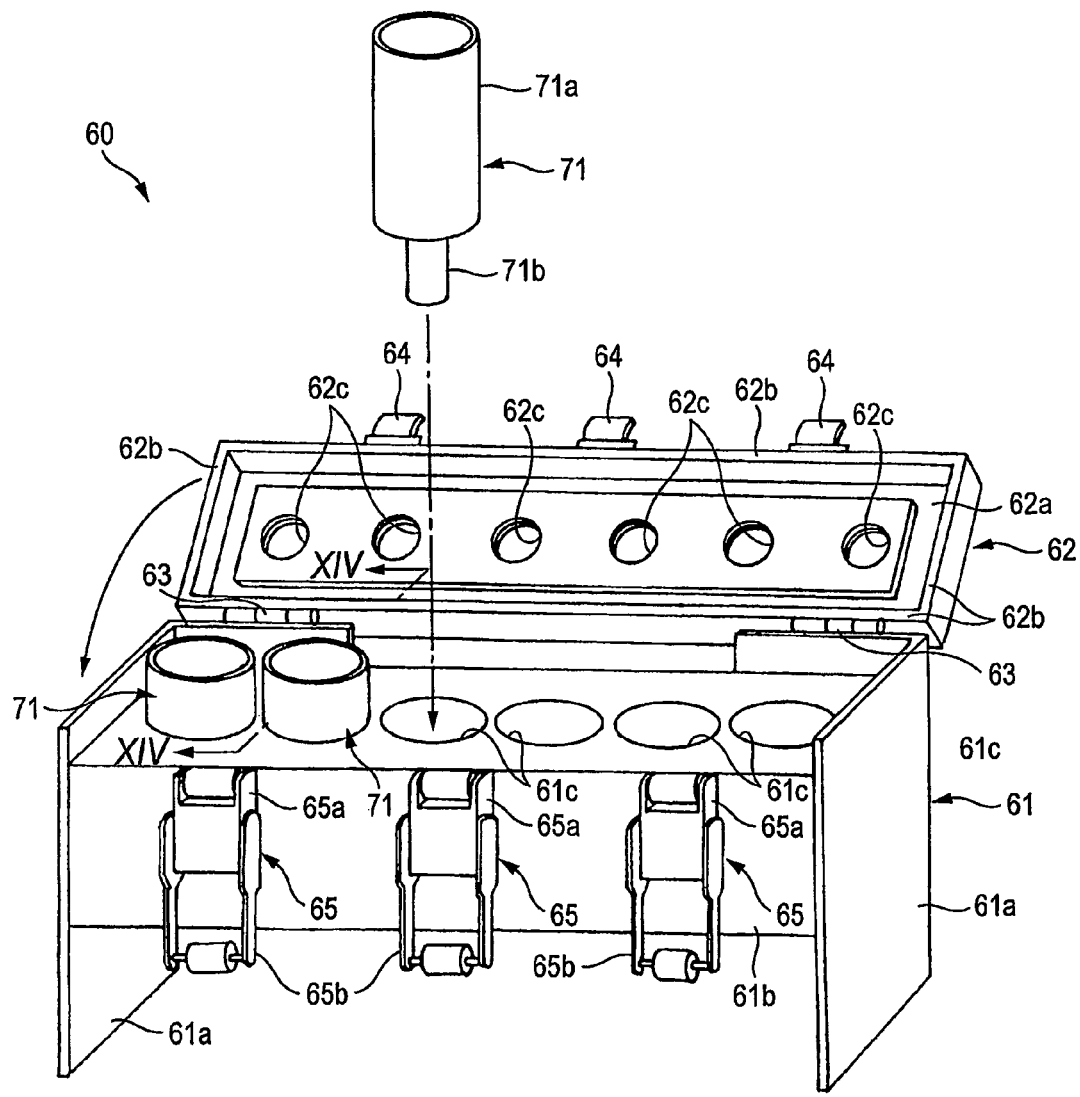
FIG. 13 is a perspective view showing a cartridge retaining mechanism of a sixth embodiment.
Figure 14:
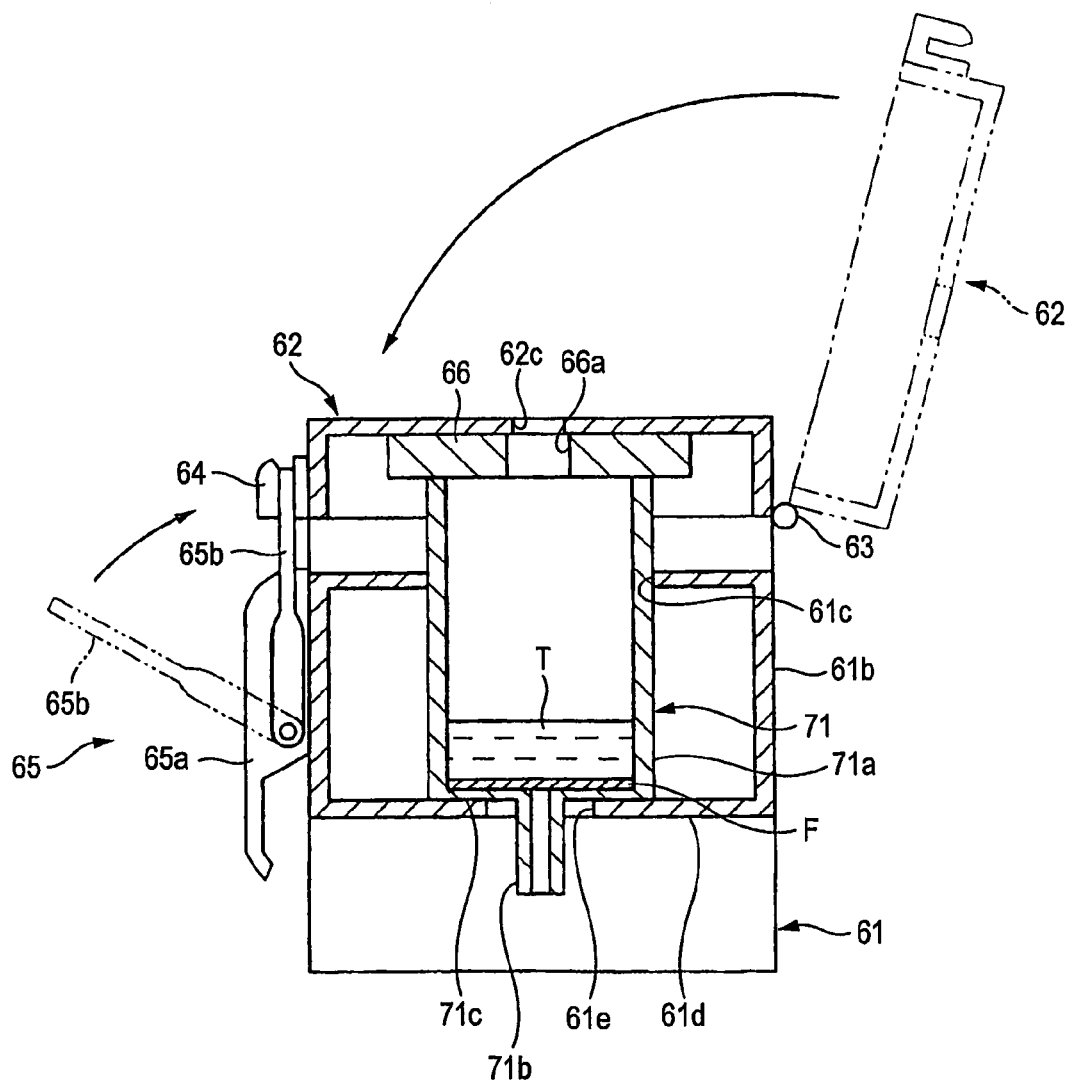
FIG. 14 is a cross sectional view on line XIVA-XIVA in FIG. 13.
Figure 15:
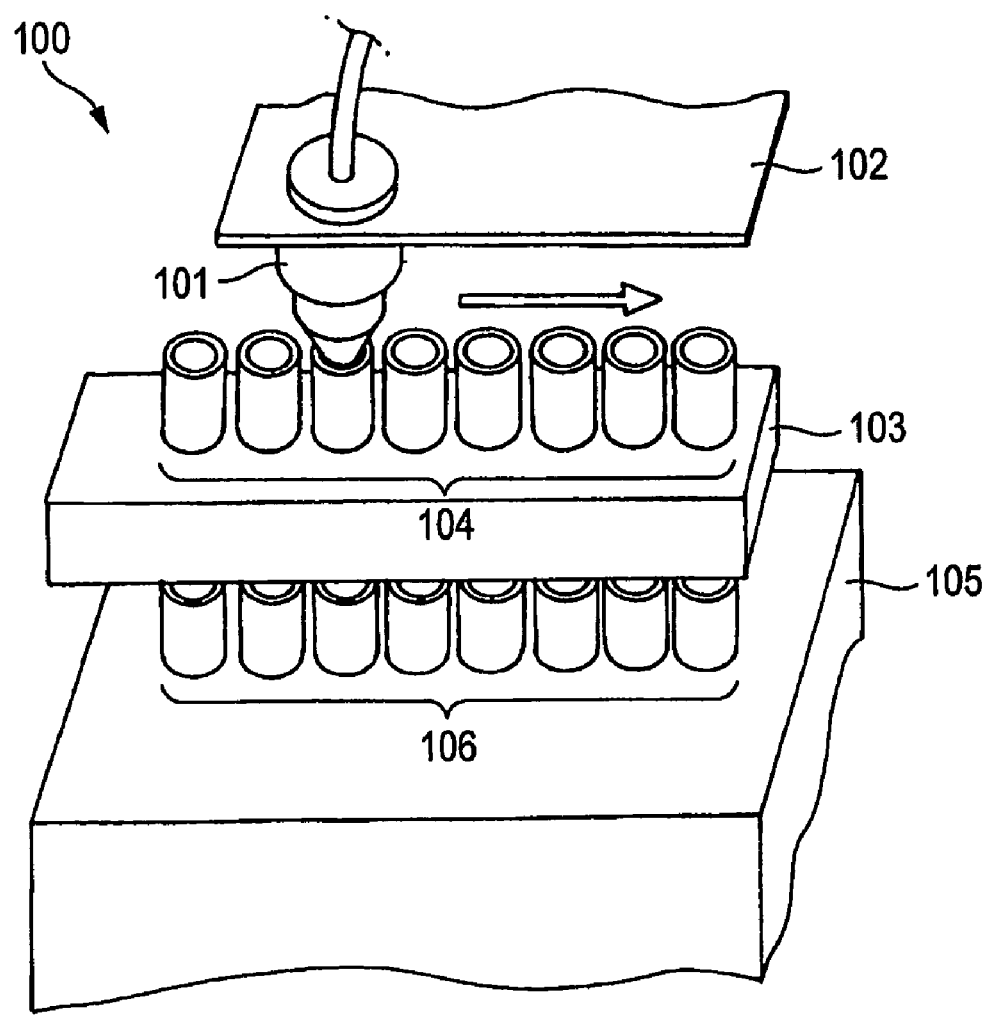
FIG. 15 is a schematic illustration showing an automatic nucleic acid extracting system.
Figure 16:
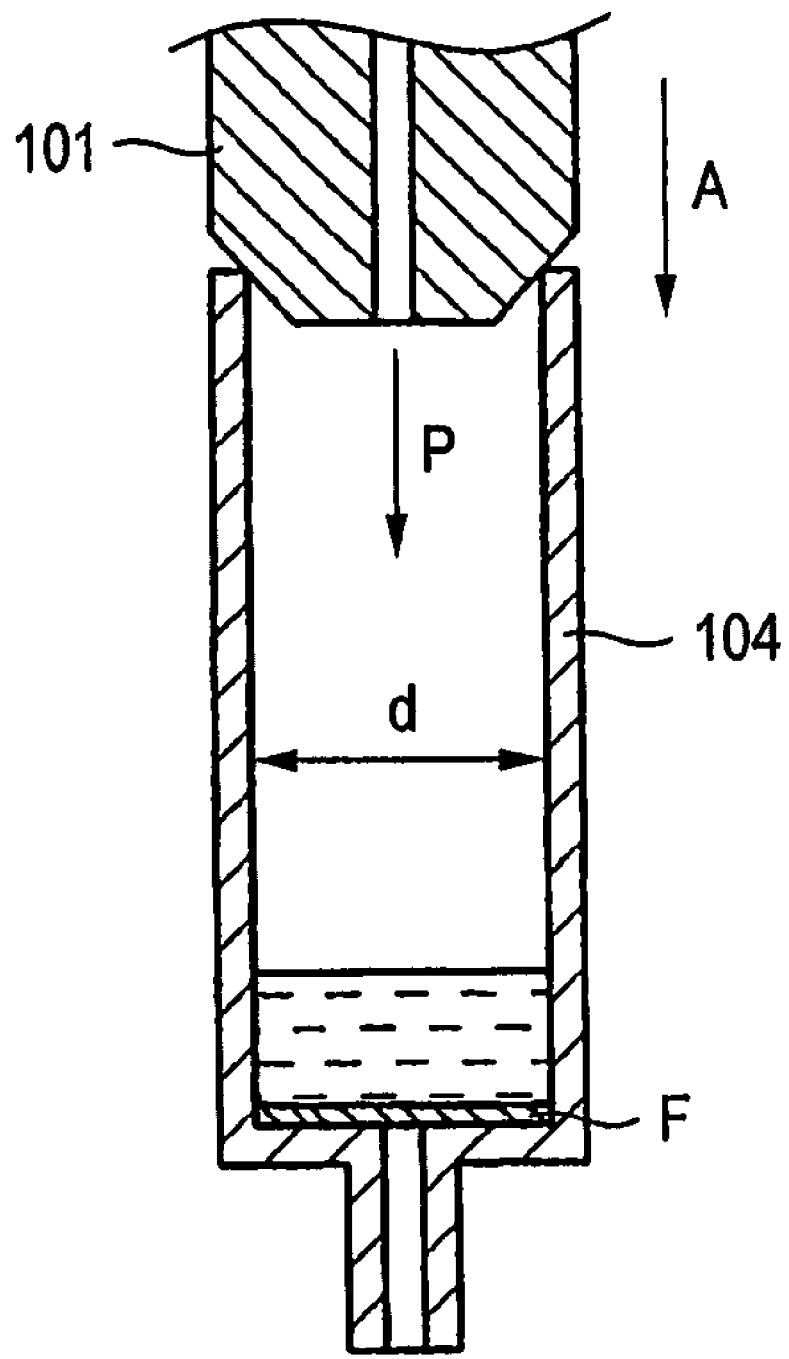
FIG. 16 is a cross sectional view showing the state where pressurized air is fed to a cartridge, wherein 10, 20, 30, 40, 50, 60 each denotes a cartridge retaining mechanism; 11, 21, 31, 41, 71 each denotes a cartridge; 12, 22, 32, 42, 61b each denotes a housing part; 13, 23, 33, 43, 62 each denotes a pressure-proof retaining part; F denotes a nucleic acid-adsorbing solid carrier; and T denotes a solution.

A sixth embodiment of the cartridge retaining mechanism according to the invention will be described. FIG. 13 is a perspective view showing the cartridge retaining mechanism of the embodiment, and FIG. 14 is a cross sectional view on line XIVA-XIVA in FIG. 13.

As shown in FIG. 13, the cartridge retaining mechanism 60 retains plural (six in the embodiment) cartridges 71 in an aligned state as one unit, and feeds pressurized air to the respective cartridges 71 with airtightness thereof ensured.

The cartridge retaining mechanism 60 has a main body 61 and a pressure-proof retaining part 62 in a lid form, which is openably mounted on the main body 61 through a hinge part 63.

The main body 61 has a pair of side plates 61a and a supporting part 61b fixed between the side plates 61a. The supporting part 61b constitutes a chassis in a substantially rectangular form as viewed on the cross section on line XIVA-XIVA, and has formed on the upper surface thereof plural installation openings 61c for installing the cartridges 71. The upper end of the side plate 61a extends upward beyond the upper surface of the supporting part 61b, and the pressure-proof retaining part 62 is in contact with the upper end upon closing the pressure-proof retaining part 62 onto the supporting part 61b. As shown in FIG. 14, a through hole 61e, through which a discharging part 71b of the cartridge 71 is inserted, is formed on the lower surface 61b of the supporting part 61b.

The pressure-proof retaining part 62 has an upper panel 62a having a substantially rectangular form and side panels 62b set up perpendicularly from two major edges and two minor edges of the upper panel 62a. One of the two side panels 62b set up from the two major edges is connected to the main body 61 through the hinge part 63.

On an outer surface of one of the two side panels 62b set up from the two major edges that is not connected to the main body 61, plural (three in the embodiment) engaging projections 64 are provided with certain intervals in the longitudinal direction of the side panel 62b.

On the supporting part 61b of the main body 61, plural (three in the embodiment) engagement driving members 65 are provided. The engagement driving member 65 has an engagement base end 65a fixed to the supporting part 61b and an engagement hook part 65b, one end of which is connected to the engagement base end 65, capable of being rotated with the fixed end as center as shown by the arrow in FIG. 14 and capable of being engaged with the engaging projection 64 of the pressure-proof retaining part 62.

The upper panel 62a is provided with nozzle receiving openings 62c, onto which pressure nozzles of the nucleic acid extracting apparatus are pressed. A gasket part 66 in a plate form is provided on the inner surface of the upper panel 62a. In the gasket part 66, connecting parts 66a connected to the nozzle receiving openings 62c of the upper panel 62a, respectively, are formed at positions corresponding to the nozzle receiving openings 62c.

In the cartridge retaining mechanism 60, the cartridge 71 is inserted into the installation opening 61c formed in the supporting part 61b of the main body 61 to insert the discharging part 71b into the through hole 61e on the lower surface 61d. Thereafter, the pressure-proof retaining part 62 is closed, and the gasket part 66 is made in contact with the open end of the cylindrical body 71a of the cartridge 71. The engagement hook part 65b of the supporting part 61b is then pulled upward to engage with the engaging projection 64 of the pressure-proof retaining part 62. As a result, the cartridge 71 is can be retained. between the supporting part 61b and the pressure-proof retaining part 62.

Upon feeding pressurized air, the pressure nozzle is pressed from above onto the nozzle receiving opening 62c of the pressure-proof retaining part 62, and pressurized air is fed to the interior of the cartridge 71 through the connecting part 66a. The pressure inside the cartridge 71 is increased by feeding pressurized air thereto, and the pressure-proof retaining part 62 receives an upward force. However, since the pressure-proof retaining part 62 is fixed to the supporting part 61b through the engaging members 65, the adhesion force between the gasket part 66 of the pressure-proof retaining part 62 and the cartridge 71 can be prevented from being lowered to prevent pressurized air from being leaked, whereby the solution T in the cartridge 71 can be stably discharged from the discharging part 71b.

Therefore, by equipping the aforementioned cartridge retaining mechanism 60 in the nucleic acid extracting apparatus, a cartridge 71 having a large diameter can be employed without modification of the pressing mechanism of the pressure nozzle, and a solution can be stably discharged to a recovering container or a waste liquor container without leakage of pressurized air.

The nucleic acid-adsorbing porous membrane (nucleic acid-adsorbing porous material) equipped in the cartridge in the aforementioned embodiments will be described in detail.

The nucleic acid-adsorbing porous membrane incorporated in the cartridge is basically a porous material, through which a nucleic acid can be passed. The surface 15 thereof has a function of adsorbing a nucleic acid in a sample solution through chemical bonding power, and retains adsorption upon rinsing with a rinsing solution but releases the nucleic acid upon recovering with a recovering solution by reducing the adsorbing power.

The nucleic acid-adsorbing porous membrane incorporated in the nucleic acid extracting cartridge such a porous membrane adsorbing a nucleic acid through mutual action that ionic bond does substantially not contribute to. This means that the porous membrane is not ionized under the using conditions, and it is expected that a nucleic acid and the porous membrane attract each other by changing the polarity of the environment. According to the constitution, a nucleic acid can be isolated and purified with excellent separation performance and good rinsing efficiency. In a preferred embodiment, the nucleic acid-adsorbing porous membrane is a porous membrane having a hydrophilic group, and in this case, it is expected that a nucleic acid and the hydrophilic group of the porous membrane attract each other by changing the polarity of the environment.

The porous membrane having a hydrophilic group means a porous membrane formed with a material that has a hydrophilic group by itself, or a porous membrane having a hydrophilic group introduced thereto by treating or coating a material constituting the porous membrane. The material constituting the porous membrane may be either an organic material or an inorganic material. Examples thereof include a porous membrane formed of an organic material having a hydrophilic group by itself, a porous membrane having a hydrophilic group introduced thereto by treating an organic material having no hydrophilic group, a porous membrane obtained by coating a porous membrane formed of an organic material having no hydrophilic group with a material having a hydrophilic group, a porous membrane formed of an inorganic material having a hydrophilic group by itself, a porous membrane having a hydrophilic group introduced thereto by treating an inorganic material having no hydrophilic group, and a porous membrane obtained by coating a porous membrane formed of an inorganic material having no hydrophilic group with a material having a hydrophilic group. In consideration of facility of processing, an organic material, such as an organic high polymer, is preferably used as a material for forming the porous membrane.

The hydrophilic group herein designates a polar group (atomic group) capable of exerting mutual action with water and includes all groups (atomic groups) that is capable of contributing to adsorption of a nucleic acid. The hydrophilic group is preferably a group having a moderate interaction with water (see the term "groups having less strong hydrophilicity" in article "hydrophilic group" in Kagaku Daijiten (Comprehensive Dictionary of Chemistry), published by Kyoritsu Shuppan Co., Ltd.). Examples thereof include a hydroxyl group, a carboxyl group, a cyano group, an oxyethylene group, an amino group and an amide group, and preferred examples thereof include a hydroxyl group.

Examples of the porous membrane having a hydrophilic group that can be used in the invention include a porous material formed of an organic material having an amide group. Preferred examples of the organic material having an amide group include polyamide. Examples of the polyamide include fibroin, polyamino acid, polypeptide, nylon 46, nylon 66, nylon 610, nylon 612, nylon 6, nylon 7, nylon 11 and nylon 12, but the invention is not limited thereto. Modified nylon, such as N-methyl modified nylon, N-alkoxymethyl modified nylon and N-alkylthiomethyl modified nylon, can also be used. Examples of the polyamide porous membrane include those obtained by using the materials and methods disclosed in U.S. Pat. Nos. 2,783,894, 3,408,315, 4,340,479, 4,340,480 and 4,450,126, German Patent No. 3,138,525, and JP-A-58-37842, but the invention is not limited thereto.

Examples of the porous membrane formed of an organic group having a hydroxyl group that can be used in the invention include porous membranes formed of polyhydroxyethyl acrylate, polyhydroxyethyl methacrylate, polyvinyl alcohol, polyvinylpyrrolidone, polyacrylic acid, polymethacrylic acid, polyoxyethylene, acetylcellulose, or a polysaccharide, such as a mixture of plural kinds of acetylcellulose having different acetyl values, and in particular, a porous membrane of an organic material having a polysaccharide structure is preferably used.

Other preferred examples of the organic material for the porous membrane include a saponification product of a polymer of vinyl acylate and a saponification product of a copolymer or two or more monomers containing at least a monomer unit of vinyl acylate. The saponification product of a polymer of vinyl acylate and the saponification product of a copolymer or two or more monomers containing at least a monomer unit of vinyl acylate in an amount of 1% by mole or more are preferred, and the acyl group of the vinyl acylate is preferably at least one selected from an acetyl group, a propyonyl group, a butyloyl group, a valeryl group, a heptanoyl group, an octanoyl group, a decanoyl group, a dodecanoyl group, a tridecanoyl group, a hexadecanoyl group and an octadecanoyl group.

Examples of the polysaccharide structure include cellulose, hemicellulose, dextran, agarose, dextrin, amylose, amylopectin, starch, glycogen, pullulan, mannan, glucomannan, lichenin, isolichenin, laminarin, carrageenan, xylan, fructan, alginic acid, hyaluronic acid, chondroitin, chitin and chitosan. Examples thereof further include derivatives of these polysaccharide structures, and in particular, ester derivatives are preferably used. The invention is not limited to these materials, but any polysaccharide structure and any derivative thereof may be used.

Saponification products of the ester derivatives of the aforementioned polysaccharide structures may further be preferably used.

The ester of the ester derivative of the polysaccharide structure is preferably at least one selected from a carboxylate ester, a nitrate ester, a sulfate ester, a sulfonate ester, a phosphate ester, a phosphonate ester and a pyrophosphate ester. Saponification products of one of the polysaccharide structures having a carboxylate ester, a nitrate ester, a sulfate ester, a sulfonate ester, a phosphate ester, a phosphonate ester and a pyrophosphate ester can also be preferably used.

The carboxylate ester of one of the polysaccharide structures is preferably at least one selected from an alkylcarbonyl ester, an alkenylcarbonyl ester, an aromatic carbonyl ester and an aromatic alkylcarbonyl ester. Saponification products of one of the polysaccharide structures having an alkylcarbonyl ester, an alkenylcarbonyl ester, an aromatic carbonyl ester and an aromatic alkylcarbonyl ester can also be preferably used.

The ester group of the alkylcarbonyl ester of one of the polysaccharide structures is preferably at least one selected from an acetyl group, a propyonyl group, a butyloyl group, a valeryl group, a heptanoyl group, an octanoyl group, a decanoyl group, a dodecanoyl group, a tridecanoyl group, a hexadecanoyl group and an octadecanoyl group. Saponification products of one of the polysaccharide structures having an acetyl group, a propyonyl group, a butyloyl group, a valeryl group, a heptanoyl group, an octanoyl group, a decanoyl group, a dodecanoyl group, a tridecanoyl group, a hexadecanoyl group and an octadecanoyl group can also be preferably used.

The ester group of the alkenylcarbonyl ester of one of the polysaccharide structures is preferably at least one selected from an acrylic group and a methacrylic group. Saponification products of one of the polysaccharide structures having an acrylic group and a methacrylic group can also be preferably used.

The ester group of the aromatic carbonyl ester of one of the polysaccharide structures is preferably at least one selected from a benzoyl group and a naphthaloyl group. Saponification products of one of the polysaccharide structures having a benzoyl group and a naphthaloyl group can also be preferably used.

As the nitrate ester of one of the polysaccharide structures, nitrocellulose, nitrohemicellulose, nitrodextran, nitroagarose, nitrodextrin, nitroamylose, nitroamylopectin, nitroglycogen, nitropullulan, nitromannan, nitroglucomannan, nitrolichenin, nitroisolichenin, nitrolaminarin, nitrocarrageenan, nitroxylan, nitrofructan, nitroalginic acid, nitrohyaluronic acid, nitrochondroitin, nitrochitin and nitrochitosan are preferably used.

Saponification products of nitrocellulose, nitrohemicellulose, nitrodextran, nitroagarose, nitrodextrin, nitroamylose, nitroamylopectin, nitroglycogen, nitropullulan, nitromannan, nitroglucomannan, nitrolichenin, nitroisolichenin, nitrolaminarin, nitrocarrageenan, nitroxylan, nitrofructan, nitroalginic acid, nitrohyaluronic acid, nitrochondroitin, nitrochitin and nitrochitosan are also preferably used.

As the sulfate ester of one of the polysaccharide structures, cellulose sulfate, hemicellulose sulfate, dextran sulfate, agarose sulfate, dextrin sulfate, amylose sulfate, amylopectin sulfate, glycogen sulfate, pullulan sulfate, mannan sulfate, glucomannan sulfate, lichenin sulfate, isolichenin sulfate, laminarin sulfate, carrageenan sulfate, xylan sulfate, fructan sulfate, alginic acid sulfate, hyaluronic acid sulfate, chondroitin sulfate, chitin sulfate and chitosan sulfate are preferably used. Saponification products of cellulose sulfate, hemicellulose sulfate, dextran sulfate, agarose sulfate, dextrin sulfate, amylose sulfate, amylopectin sulfate, glycogen sulfate, pullulan sulfate, mannan sulfate, glucomannan sulfate, lichenin sulfate, isolichenin sulfate, laminarin sulfate, carrageenan sulfate, xylan sulfate, fructan sulfate, alginic acid sulfate, hyaluronic acid sulfate, chondroitin sulfate, chitin sulfate and chitosan sulfate are also preferably used.

The sulfonate ester of one of the polysaccharide structures is preferably at least one selected from an alkyl sulfonate ester, an alkenyl sulfonate ester, an aromatic sulfonate ester and an aromatic alkyl sulfonate ester. Saponification products of one of the polysaccharide structures having an alkyl sulfonate ester, an alkenyl sulfonate ester, an aromatic sulfonate ester and an aromatic alkyl sulfonate ester can also be preferably used.

As the phosphate ester of one of the polysaccharide structures, cellulose phosphate, hemicellulose phosphate, dextran phosphate, agarose phosphate, dextrin phosphate, amylose phosphate, amylopectin phosphate, glycogen phosphate, pullulan phosphate, mannan phosphate, glucomannan phosphate, lichenin phosphate, isolichenin phosphate, laminarin phosphate, carrageenan phosphate, xylan phosphate, fructan phosphate, alginic acid phosphate, hyaluronic acid phosphate, chondroitin phosphate, chitin phosphate and chitosan phosphate are preferably used. Saponification products of cellulose phosphate, hemicellulose phosphate, dextran phosphate, agarose phosphate, dextrin phosphate, amylose phosphate, amylopectin phosphate, glycogen phosphate, pullulan phosphate, mannan phosphate, glucomannan phosphate, lichenin phosphate, isolichenin phosphate, laminarin phosphate, carrageenan phosphate, xylan phosphate, fructan phosphate, alginic acid phosphate, hyaluronic acid phosphate, chondroitin phosphate, chitin phosphate and chitosan phosphate are also preferably used.

As the phosphonate ester of one of the polysaccharide structures, cellulose phosphonate, hemicellulose phosphonate, dextran phosphonate, agarose phosphonate, dextrin phosphonate, amylose phosphonate, amylopectin phosphonate, glycogen phosphonate, pullulan phosphonate, mannan phosphonate, glucomannan phosphonate, lichenin phosphonate, isolichenin phosphonate, laminarin phosphonate, carrageenan phosphonate, xylan phosphonate, fructan phosphonate, alginic acid phosphonate, hyaluronic acid phosphonate, chondroitin phosphonate, chitin phosphonate and chitosan phosphonate are preferably used. Saponification products of cellulose phosphonate, hemicellulose phosphonate, dextran phosphonate, agarose phosphonate, dextrin phosphonate, amylose phosphonate, amylopectin phosphonate, glycogen phosphonate, pullulan phosphonate, mannan phosphonate, glucomannan phosphonate, lichenin phosphonate, isolichenin phosphonate, laminarin phosphonate, carrageenan phosphonate, xylan phosphonate, fructan phosphonate, alginic acid phosphonate, hyaluronic acid phosphonate, chondroitin phosphonate, chitin phosphonate and chitosan phosphonate are also preferably used.

As the phosphate ester of one of the polysaccharide structures, cellulose pyrophosphate, hemicellulose pyrophosphate, dextran pyrophosphate, agarose pyrophosphate, dextrin pyrophosphate, amylose pyrophosphate, amylopectin pyrophosphate, glycogen pyrophosphate, pullulan pyrophosphate, mannan pyrophosphate, glucomannan pyrophosphate, lichenin pyrophosphate, isolichenin pyrophosphate, laminarin pyrophosphate, carrageenan pyrophosphate, xylan pyrophosphate, fructan pyrophosphate, alginic acid pyrophosphate, hyaluronic acid pyrophosphate, chondroitin pyrophosphate, chitin pyrophosphate and chitosan pyrophosphate are preferably used. Saponification products of cellulose pyrophosphate, hemicellulose pyrophosphate, dextran pyrophosphate, agarose pyrophosphate, dextrin pyrophosphate, amylose pyrophosphate, amylopectin pyrophosphate, glycogen pyrophosphate, pullulan pyrophosphate, mannan pyrophosphate, glucomannan pyrophosphate, lichenin pyrophosphate, isolichenin pyrophosphate, laminarin pyrophosphate, carrageenan pyrophosphate, xylan pyrophosphate, fructan pyrophosphate, alginic acid pyrophosphate, hyaluronic acid pyrophosphate, chondroitin pyrophosphate, chitin pyrophosphate and chitosan pyrophosphate are also preferably used.

As the ether derivative of one of the polysaccharide structures, methyl cellulose, ethyl cellulose, carboxymethyl cellulose, carboxyethyl cellulose, carboxyethyl carbamoylethyl cellulose, hydroxymethyl cellulose, hydroxyethyl cellulose, hydroxypropyl cellulose, hydroxypropylmethyl cellulose, hydroxyethylmethyl cellulose, cyanoethyl cellulose and carbamoylethyl cellulose can be preferably used, but the invention is not limited thereto. Hydroxymethyl cellulose and hydroxyethyl cellulose are preferably used.

One of the polysaccharide structures having hydroxyl groups that are halogenated in an arbitrary substitution degree may also be preferably used.

The cellulose ester derivative will be described below. Examples of cellulose as a raw material of the cellulose ester derivative include natural cellulose, such as cotton linter, wood pulp (e.g., hardwood pulp and softwood pulp), hemp, and cellulose formed on culturing acetic acid bacteria, and materials obtained by subjecting the natural cellulose to acid hydrolysis, mechanical pulverization, blasting treatment, and extruding treatment under high temperatures, so as to adjust the polymerization degree thereof. Cellulose ester derivatives obtained from any raw material cellulose can be used, and may be used after mixing in some cases. Detailed description of the raw material cellulose are found, for example, in Marusawa and Uda, Plastic Zairyo Koza (Lectures on Plastic Materials) vol. 17, Seniso-kei Jusi (Cellulose Resins), published by Nikkan Kogyo Shimbun, Ltd. (1970).

According to the aforementioned literature, the molecular weight of cellulose varies over a wide range. For example, natural cellulose has a molecular weight of from 600,000 to 1,500,000 (from 3,500 to 10,000 in terms of polymerization degree), refined linter has a molecular weight of from 80,000 to 500,000 (from 500 to 3,000 in terms of polymerization degree) and wood pulp has a molecular weight of from 80,000 to 1,340,000 (from 500 to 2,100 in terms of polymerization degree). The molecular weight largely influences the strength property of cellulose or a derivative thereof When the molecular weight is decreased, the mechanical strength thereof is suddenly decreased beyond a certain polymerization degree, but such a material may be used as a raw material of the nucleic acid-adsorbing porous membrane in the invention without any problem.

As one example of the nucleic acid-adsorbing porous membrane, a porous membrane of a cellulose derivative obtained by esterification of cellulose can be used, but the aforementioned preferred species of cellulose may not be used as they are, but are used as purified linter or purified high-quality wood pulp after purifying linter or pulp. Linter contains short fibers among cotton fibers of cotton seeds and has a large content of α-cellulose (for example from 88 to 92% by mass) and a high purity with less impurities. Purified linter can be obtained by subjecting crude linter to garbage collection, alkali steaming, bleaching, acid treatment, dehydration and drying. (In this specification, % by mass is equal to % by weight.) The details of the process are disclosed in Marusawa and Uda, Plastic Zairyo Koza (Lectures on Plastic Materials) vol. 17, Seniso-kei Jusi (Cellulose Resins), published by Nikkan Kogyo Shimbun, Ltd. (1970) on pages 25 to 28, and the characteristics thereof are disclosed in Table 2.3 of the literature, by which purified linter that can be preferably used in the invention can be obtained.

Purified pulp is also disclosed in the same literature on pages 28 to 32, and the characteristics thereof are disclosed in Table 2.4. Pulp purified by the disclosed methods is also preferably used as a raw material of the cellulose ester derivative. It is preferred that cotton linter and wood pulp, which have been purified, are used after mixing, and the mixing ratio is preferably from 5/95 to 95/5, and more preferably 10/90 to 90/10, while it is not particularly limited thereto. The solubility of the material is improved by mixing, whereby the surface property and the mechanical characteristics of the porous membrane of the cellulose ester derivative can be improved.

In the materials, the α-cellulose content, which is an index of purity of pulp, can be selected, for example, from a range of about from 80 to 100% by mass, and is generally about from 85 to 98% in wood pulp. Low purity pulp, for example, pulp having an α-cellulose content of about from 80 to 96% (particularly from 92 to 96%) may also be used in the invention. Among these kinds of pulp, wood pulp is generally used.

In the nucleic acid-adsorbing porous membrane of the invention, the neutral constituent sugar component in pulp of cotton, which mainly contains glucose, may contain mannose and xylose as described in JP-A-11-130301. The ratio thereof is not particularly limited, and the ratio of mannose/xylose (molar ratio) is generally from 0.35/1 to 3.0/1, preferably from 0.35/1 to 2.5/1, and more preferably from 0.35/1 to 2/1. In the cellulose triacetate thus produced in this case, the total content of mannose and xylose is generally from 0.01 to 5% by mole, and preferably from 0.1 to 4% by mole. Mannose and xylose herein are major constituent sugars of hemicellulose (such as xylan and glucomannan) contained in pulp. The constituent sugar components of the raw material pulp and the cellulose ester derivative thus obtained (e.g., cellulose triacetate) can be analyzed by the method disclosed in JP-A-11-130301.

As the porous membrane of cellulose, a porous membrane of regenerated cellulose may be preferably used. Examples of the regenerated cellulose include a material obtained by converting a surface of the whole of a solid of acetylcellulose to cellulose through saponification, a material produced from a copper ammonia solution of cellulose, a material produced from a viscose solution of cellulose, and a material produced from an alkali solution of cellulose, which are different from original cellulose in crystalline state and the like. Cellulose includes crystal forms I, II, III and IV. Any of crystal forms can be preferably used in the invention, and cellulose used in the invention may contain the crystal forms I, II, III and IV in any proportions. As a regenerated cellulose porous membrane produced from an acetylcellulose porous membrane, those obtained by the raw materials and the methods disclosed in JP-B-45-4633 and JP-A-56-100604 may be used, but the invention is not limited thereto. As a regenerated cellulose porous membrane produced from a copper ammonia solution of cellulose, those obtained by the raw materials and the methods disclosed in JP-A-58-89625, JP-A-58-89626, JP-A-58-89627, JP-A-58-89628, JP-A-59-45333, JP-A-59-45334, JP-A-59-199728, JP-A-61-274707, JP-A-62-1403, JP-A-63-161972 and JP-A-7-330945 may be used, but the invention is not limited thereto. A regenerated cellulose porous membrane can be obtained by modifying the composition of the reaction solution and the coagulation method of a viscose solution obtained by effecting an alkali and carbon disulfide to cellulose, and can be used in the invention. As a regenerated cellulose porous membrane produced from an alkali solution of cellulose, those obtained by the raw materials and the methods disclosed in JP-A-62-240328, JP-A-62-240329 and JP-A-1-188539 may be used, but the invention is not limited thereto.

In the nucleic acid-adsorbing porous membrane of the invention, the cellulose ester derivative preferably has a viscosity average molecular weight of from 200 to 3,000. The cellulose derivative preferably has a ratio of weight average molecular weight and number average molecular weight of from 0.8 to 2. The cellulose ester derivative preferably contains an acid having an acid dissociation exponent of from 1.93 to 4.5 or a salt thereof.

The cellulose ester derivative preferably has a content of remaining acetic acid or a fatty acid having from 3 to 22 carbon atoms of 0.5% by mass or less. The cellulose ester derivative preferably contains at least one kind of an alkali metal and/or an alkaline earth metal in an amount of from 1 ppb to 10,000 ppm. The cellulose acylate preferably contains at least one kind of aluminum, bismuth, silicon and a heavy metal (such as chromium, manganese, iron, cobalt, nickel, copper, zinc, arsenic, silver, cadmium, tin, antimony, gold, platinum, mercury and lead) in an amount of from 1 ppb to 1,000 ppm.

Particularly preferred examples of the porous film of a cellulose ester derivative include a porous membrane of an organic high polymer composed of a mixture of plural kinds of acetylcellulose different from each other in acetyl value. As the mixture of plural kinds of acetylcellulose different from each other in acetyl value, a mixture of triacetylcellulose and monoacetylcellulose, a mixture of triacetylcellulose, diacetylcellulose and monoacetylcellulose, and a mixture of diacetylcellulose and monoacetylcellulose are preferably used. In particular, a mixture of triacetylcellulose and diacetylcellulose is preferably used. The mixing ratio (mass ratio) of triacetylcellulose and diacetylcellulose is preferably from 99/1 to 1/99, and more preferably from 90/10 to 50/50.

As the cellulose ester derivative, cellulose ester derivatives disclosed in JP-A-10-45803, JP-A-11-269304, JP-A-8-231761, JP-A-10-60170, JP-A-9-40792, JP-A-11-5851, JP-A-11-269304, JP-A-9-90101, JP-A-57-182737, JP-A-4-277530, JP-A-11-292989, JP-A-12-131524 and JP-A-12-137115 are preferably used. The nucleic acid-adsorbing porous membrane of the invention is not limited to these materials.

X-ray analysis is used as a measure for evaluating structures of cellulose. According to the analysis, cellulose molecules are aligned in parallel in the direction of fiber axis and attract each other through hydrogen bond, and one unit cell is formed of a cellbiose unit of five cellulose molecules. The X-ray method shows that the degree of crystallinity of natural cellulose is about 70%, and these kinds of cellulose can be used for producing the cellulose ester derivative in the invention.

There have been various analysis methods for cellulose used in the invention, which are described in detail in ASTM Standard Part 15, TAPPI Standard (Technical Association of the Pulp and Paper Industry), JIS P8101. The measuring items includes an ash content, a content of calcium oxide and magnesium oxide, α-cellulose, β-cellulose and a copper value.

Saponification means an operation of making an ester derivative in contact with a saponification treatment solution (such as a sodium hydroxide aqueous solution). According to the operation, the ester part of the ester derivative having been in contact with the saponification treatment solution is hydrolyzed to introduce a hydroxyl group. In order to change the saponification degree, the saponification treatment is carried out by changing the concentration of sodium hydroxide, the treating temperature and the treating time. The saponification degree can be easily measured by NMR, IR or IPS (for example, through the decrement of the peak of a carbonyl group).

Specific examples of the porous membrane of an organic material having a polysaccharide structure include a surface-saponification product of acetylcellulose disclosed in JP-A-2003-128691. The surface-saponification product of acetylcellulose is a material obtained by subjecting plural kinds of acetylcellulose different in acetyl value to a saponification treatment, and a saponification product of a mixture of triacetylcellulose and diacetylcellulose, a saponification product of a mixture of triacetylcellulose and monoacetylcellulose, a saponification product of a mixture of triacetylcellulose, diacetylcellulose and monoacetylcellulose, and a saponification product of a mixture of diacetylcellulose and monoacetylcellulose are preferably used. The mixing ratio (mass ratio) of triacetylcellulose and diacetylcellulose is preferably from 99/1 to 1/99, and more preferably from 90/10 to 50/50. In this case, the amount (density) of hydroxyl groups on the surface can be controlled by the extent of the saponification treatment (saponification degree). In order to improve the separation efficiency of a nucleic acid, it is preferred that the amount (density) of hydroxyl group is preferably higher. For example, in the case of acetylcellulose, such as triacetylcellulose, the saponification degree (surface saponification degree) is preferably about 5% or more, and more preferably 10% or more. In order to increase the surface area of an organic high polymer having a hydroxyl group, it is preferred that a porous membrane of acetylcellulose is subjected to a saponification treatment. The operation is preferably employed since the porous membrane can be produced without discrimination between front and back surfaces of the membrane by using a porous membrane having front and back surfaces symmetrical with each other, and the risk of clogging can be reduced by using a porous membrane having front and back surfaces asymmetrical with each other.

As a method for introducing a hydrophilic group to a porous membrane of an organic material having no hydrophilic group, a graft polymer chain having a hydrophilic group in the polymer chain or a side chain thereof is bonded to the porous membrane. The method of bonding the graft polymer chain to the porous membrane of the organic material includes two methods, i.e., a method of chemically bonding the graft polymer chain to the porous membrane, and a method of polymerizing a compound having a polymerizable double bond from the porous membrane as a starting point to form the graft polymer chain.

In the method of attaching the graft polymer chain to the porous membrane through chemical bond, a polymer having a functional group capable of reacting with the porous membrane at an end or a side chain of the polymer is used, and the functional group and a functional group on the porous membrane are subjected to chemical reaction to achieve graft reaction. The functional group capable of reacting the porous membrane is not particularly limited as far as it is capable of reacting the functional group on the porous membrane, and examples thereof include a silane coupling group, such as alkoxysilane, an isocyanate group, an amino group, a hydroxyl group, a carboxyl group, a carbonyl group, a sulfonic acid group, a phosphoric acid group, an epoxy group, an allyl group, a methacryloyl group, an acryloyl group, an amide group, a hydrazide group, an aldehyde group, a thiol group and a succinimide group.

Examples of a compound that is particularly useful as the polymer having a reactive functional group at an end or a side chain of the polymer include a polymer having a trialkoxysilyl group at an end of the polymer, a polymer having an amino group at an end of the polymer, a polymer having a carboxyl group at an end of the polymer, a polymer having an epoxy group at an end of the polymer, and a polymer having an isocyanate group at an end of the polymer. The polymer used herein is not particularly limited as far as it has such a hydrophilic group that contributes to adsorption of a nucleic acid, and specific examples thereof include polyhydroxyethyl acrylate and polyhydroxyethyl methacrylate, and salts thereof, polyvinyl alcohol, polyvinyl pyrrolidone, polyacrylic acid and polymethacrylic acid, and salts thereof, polyoxyethylene, polylactic acid, polyketone, polyetherimide, polyamideimide, polyphenylene sulfone, polyphenylene sulfide sulfone, nylon, N-methyl modified nylon, N-alkoxymethyl modified nylon, N-alkylthiomethyl modified nylon, polysulfone, polyethersulfone, polyarylsulfone, polyallylsulfone and polyurethane.

The method of polymerizing a compound having a polymerizable double bond from the porous membrane as a starting point to form the graft polymer chain is generally referred to as a surface graft polymerization. The surface graft polymerization method is such a method that a surface of a porous membrane as a substrate is provided with an active species by plasma irradiation, light irradiation or heating, to which a compound having a polymerizable double bond disposed to be in contact with the porous membrane is bonded through polymerization.

It is necessary that the compound useful for forming a graft polymer chain bonded to the substrate satisfies two requirements, i.e., it has a polymerizable double bond, and it has a hydrophilic group capable of contributing to adsorption of a nucleic acid. As the compound, any of polymers, oligomers and monomers having a hydrophilic group can be used as far as they have a double bond in the molecules thereof. Monomers having a hydrophilic group are particularly useful.

Specific examples of the useful monomer having a hydrophilic group include the following monomers. For example, a monomer having a hydroxyl group, such as 2-hydroxyethyl acrylate, 2-hydroxyethyl methacrylate and glycerol monomethacryate, can be preferably used. A carboxyl group-containing monomer, such as acrylic acid and methacrylic acid, and an alkali metal salt, an amine salt and an acrylamide thereof are also preferably used.

As another method for introducing a hydrophilic group to a porous membrane of an organic material having no hydrophilic group, a method of coating a material having a hydrophilic group can be employed. The material used for coating is not particularly limited as far as it has a hydrophilic group capable of contributing to adsorption of a nucleic acid, and a polymer of an organic material is preferred from the standpoint of easiness in operation. Examples of the polymer include polyhydroxyethyl acrylate and polyhydroxyethyl methacrylate, and salts thereof, polyvinyl alcohol, polyvinyl pyrrolidone, polyacrylic acid and polymethacrylic acid, and salts thereof, polyoxyethylene, acetylcellulose and a mixture of plural kinds of acetylcellulose different in acetyl value, and a polymer having a polysaccharide structure is preferred.

It is also possible that acetylcellulose or a mixture of plural kinds of acetylcellulose different in acetyl value is coated on a porous membrane of an organic material having no hydrophilic group, and then the acetylcellulose or the mixture of plural kinds of acetylcellulose different in acetyl value thus coated is subjected to a saponification treatment. In this case, the saponification degree is preferably about 5% or more, and more preferably about 10% or more.

Examples of a porous membrane of an inorganic material having a hydrophilic group include a porous membrane containing a silica compound. Examples of the porous membrane containing a silica compound include a glass filter. Examples thereof also include a porous silica thin film disclosed in Japanese Patent No. 3058342. The porous silica thin film can be produced in the following manner. An expansion solution of a cationic amphoteric substance having a bimolecular membrane is expanded on a substrate, and a solvent is removed from the liquid membrane on the substrate to prepare a multilayer bimolecular thin film of the amphoteric substance. The multilayer bimolecular thin film is made in contact with a solution containing a silica compound, and then the multilayer bimolecular thin film is removed by extraction to obtain the porous silica thin film.

The method for introducing a hydrophilic group to a porous membrane of an inorganic material having no hydrophilic group includes the following two methods, i.e., a method of chemically bonding a graft polymer chain to the porous membrane, and a method of polymerizing a monomer having a polymerizable double bond and a hydrophilic group from the porous membrane as a starting point to form a graft polymer chain.

In the method of attaching the graft polymer chain to the porous membrane through chemical bond, a functional group capable of reacting a functional group at an end of the graft polymer chain is introduced to the inorganic material, and the graft polymer is chemically bonded thereto. In the method of polymerizing a monomer having a polymerizable double bond and a hydrophilic group from the porous membrane as a starting point to form a graft polymer chain, a functional group capable of being a starting point of polymerization of the compound having a double bond is introduced to the inorganic compound.

As the graft polymer having a hydrophilic group and the monomer having a polymerizable double bond and a hydrophilic group, the graft polymers having a hydrophilic group and the monomers having a hydrophilic group and a double bond in the molecule disclosed in the method of chemically bonding the graft polymer chain to the porous membrane of an organic material having no hydrophilic group are preferably used.

As another method for introducing a hydrophilic group to a porous membrane of an inorganic material having no hydrophilic group, a method of coating a material having a hydrophilic group can be employed. The material used for coating is not particularly limited as far as it has a hydrophilic group capable of contributing to adsorption of a nucleic acid, and a polymer of an organic material is preferred from the standpoint of easiness in operation. Examples of the polymer include polyhydroxyethyl acrylate and polyhydroxyethyl methacrylate, and salts thereof, polyvinyl alcohol, polyvinyl pyrrolidone, polyacrylic acid and polymethacrylic acid, and salts thereof, polyoxyethylene, acetylcellulose and a mixture of plural kinds of acetylcellulose different in acetyl value.

Examples of the porous membrane of an inorganic material having no hydrophilic group include porous membranes obtained by processing a metal, such as aluminum, glass, cement, ceramics, such as pottery and porcelain, new ceramics, silicon, activated carbon, and aluminosilicate.

It is also possible that acetylcellulose or a mixture of plural kinds of acetylcellulose different in acetyl value is coated on a porous membrane of an inorganic material having no hydrophilic group, and then the acetylcellulose or the mixture of plural kinds of acetylcellulose different in acetyl value thus coated is subjected to a saponification treatment. In this case, the saponification degree is preferably about 5% or more, and more preferably about 10% or more.

In the preparation process of the nucleic acid-adsorbing solid carrier, various kinds of additives corresponding to purposes (such as a plasticizer, an antistatic agent, a deterioration preventing agent, an ultraviolet ray inhibitor, a surfactant, a releasing agent, a coloring agent, a reinforcing agent and a crosslinking agent) may be added. The timing of the addition may be any occasion during the dope preparing process, and the step of adding the additive may be carried out as the final step of the dope preparing process.

The nucleic acid-adsorbing solid carrier may contain a plasticizer depending on necessity. Preferred examples of the plasticizer include phosphate esters and carboxylate esters disclosed in JP-A-2002-265636, polyhydric alcohols disclosed in JP-A-2-6826, (di)pentaerythritol esters disclosed in JP-A-5-194788, JP-A-60-250053, JP-A-4-227941, JP-A-6-16869, JP-A-5-271471, JP-A-7-286068, JP-A-5-5047, JP-A-11-80381, JP-A-7-20317, JP-A-8-57879, JP-A-10-152568, JP-A-10-120824 and JP-A-11-124445, glycerol esters disclosed in JP-A-11-246704, diglycerol esters disclosed in JP-A-2000-63560, citrate esters disclosed in JP-A-11-92574, substituted phenyl phosphate esters disclosed in JP-A-11-90946, and plasticizers disclosed in JP-A-56-100604. The literatures cited herein contain various descriptions of usage and characteristics of the plasticizers, which can be preferably used in the nucleic acid-adsorbing solid carrier of the invention.

The nucleic acid-adsorbing solid carrier of the invention may contain an antistatic agent for the purpose of preventing the membrane from being charged upon handling. Preferred examples of the antistatic agent include an ionic electroconductive substance and electroconductive particles. The ionic electroconductive substance is such a substance that exhibits electroconductivity and contains ions as a carrier for carrying electricity, and examples thereof include an ionic high polymer compound. Examples of the ionic high polymer compound include anionic high polymer compounds disclosed in JP-B-49-23828, JP-B-49-23827and JP-B-47-28937, ionene polymers having a dissociation group in a main chain disclosed in JP-B-55-734, JP-A-50-54672, JP-B-59-14735, JP-B-57-18175, JP-B-57-18176 and JP-B-57-56059, and cationic pendant polymers having a cationic dissociation group on a side chain disclosed in JP-B-53-13223, JP-B-57-15376, JP-B-53-45231, JP-B-55-145783, JP-B-55-56950, JP-B-55-67746, JP-B-57-11342, JP-B-57-19735, JP-B-58-56858, JP-A-61-27853 and JP-B-62-9346. Among these, what is preferred includes a material having the electroconductive substance in a fine particle form finely dispersed in the nucleic acid-adsorbing solid carrier, which preferably contains as an electroconductive substance electroconductive fine particles of a metallic oxide or complex oxide, and an ionene electroconductive polymer or a quaternary ammonium cationic electroconductive polymer particles having intermolecular crosslinks disclosed in JP-A-9-203810. The particle diameter is preferably from 5 nm to 10 µm, and the more preferred range of the diameter depends on the species of the fine particles used. Preferred examples of the metallic oxide as the electroconductive fine particles include ZnO, $TiO_2$, $SnO_2$, $Al_2O_3$, $In_2O_3$, $SiO_2$, MgO, BaO, $MoO_2$, $V_2O_5$ and complex oxides thereof, and ZnO, $TiO_2$ and $SnO_2$ are particularly preferred. Effective examples of the material containing a hetero element include ZnO added with Al or In, $TiO_2$ added with Nb or Ta, and $SnO_2$ added with Sb, Nb or a halogen element. The addition amount of the hetero element is preferably from 0.01 to 25% by mole, and particularly preferably from 0.1 to 15% by mole. As the metallic oxide particles having electroconductivity, particles having a volume resistivity of 107 Ω·cm or less, and particularly preferably 105 Ω·cm or less, and a primary particle diameter of from 100 Å to 0.2 µm and a particular structure of a major diameter of the high order structure of from 30 nm to 6 µm are preferably contained in the nucleic acid-adsorbing solid carrier in an amount of from 0.01 to 20% in terms of volume fraction. Since the crosslinked cationic electroconductive polymer as a dispersive particle polymer has such characteristics that a cationic component can be retained inside the particles at a high concentration and a high density, it is not only excellent in electroconductivity but also free of deterioration in electroconductivity under a low relative humidity condition. The particles thereof is well dispersed in the dispersed state, but upon forming a membrane, particles exhibit good adhesiveness in the membrane forming step after flow casting, and the membrane shows a high membrane strength and excellent chemical resistance. The crosslinked cationic electroconductive polymer as a dispersive particle polymer generally has a particle size of about from 10 to 1,000 nm, and preferably from 20 to 300 nm. The dispersive particle polymer herein is such a polymer that forms a transparent or slightly turbid solution under visual observation but is observed as a particle dispersion under an electron microscope. An organic electron electroconductive organic compound may also be used. Examples thereof include polythiophene, polypyrrole, polyaniline, polyacetylene and polyphosphazene. These materials are preferably used as a complex with polystyrene sulfonic acid or perchloric acid as an acid donating material.

The nucleic acid-adsorbing solid carrier may contain a deterioration preventing agent (such as an antioxidant, a peroxide decomposing agent, a radical inhibitor, a metal inactivating agent, an acid scavenger and an amine) and an ultraviolet ray inhibitor. As the deterioration preventing agent and the ultraviolet ray inhibitor, those disclosed in JP-A-60-235852, JP-A-3-199201, JP-A-5-190707, JP-A-5-194789, JP-A-5-271471, JP-A-6-107854, JP-A-6-118233, JP-A-6-148430, JP-A-7-11056, JP-A-7-11055, JP-A-8-29619, JP-A-8-239509, JP-A-2000-204173, JP-A-5-197073, JP-A-5-194789, JP-A-6-107854, JP-A-60-235852, JP-A-12-193821, JP-A-8-29619, JP-A-6-118233, JP-A-6-148430, JP-A-2002-265636 and JP-A-5-197073 can be preferably used. Particularly preferred examples of the deterioration preventing agent include dibutylhydroxytoluene (BHT).

The addition amount of the deterioration preventing agent is preferably from 0.01 to 1% by mass, and more preferably from 0.01 to 0.08% by mass, based on the solution (dope) to be prepared. In the case where the addition amount is less than 0.01% by mass, substantially no effect of the deterioration preventing agent can be obtained. In the case where the addition amount exceeds 1% by mass, there are some cases where the deterioration preventing agent is bled out to the surface of the solid carrier. The deterioration preventing agent used in the invention is preferably a liquid at 25° C. having a boiling point of 200° C. or higher or a solid having a melting point of from 25 to 250° C., and more preferably a liquid at 25° C. having a boiling point of 250° C. or higher or a solid having a melting point of from 25 to 200° C. In the case where the deterioration preventing agent is a liquid, it can be generally purified by distillation under reduced pressure, and the pressure is preferably as high as possible, and for example, is preferably 100 Pa or less. It is particularly preferred that it is purified by using a molecular distillation apparatus. In the case where the plasticizer is a solid, it is generally purified by recrystallization using a solvent, filtration, rinsing and drying.

The nucleic acid-adsorbing solid carrier may contain a surfactant. As the surfactant, those disclosed in JP-A-2002-265636, JP-B-55-31418, Kaimen Kasseizai tou Ichiranhyo (Catalog of Surfactants, etc.), 2001 ed., published by Japan Surfactant Industry Association, and T. Karimai, Kaimen Kasseizai no Oyo (Applications of Surfactants), published by Saiwaishobo Co., Ltd. on Sep. 1, 1980 can be preferably used, but the invention is not limited thereto. In the invention, preferred surfactants are not particularly limited in species and using amount thereof, and they can be used in such an amount that provides target surface active characteristics.

The nucleic acid-adsorbing solid carrier may contain a releasing agent depending on necessity for reducing a load on releasing in the production thereof. A surfactant is effective as the releasing agent, which is not particularly limited and may be a phosphoric acid series, a sulfonic acid series, a carboxylic acid series, a nonionic series and a cationic series. These are disclosed, for example, in JP-A-6.1-243837 and JP-A-2000-99847. An acid having an acid dissociation constant pKa of from 1.93 to 4.50 (preferably from 2.0 to 4.4, more preferably from 2.2 to 4.3 (for example from 2.5 to 4.0), and particularly preferably from 2.6 to 4.3 (for example from 2.6 to 4.0) or a salt thereof disclosed in JP-A-10-316701 is preferred as the releasing agent. The salt may be either an inorganic salt or an organic salt. With respect to pKa of an acid, Kagaku Binran (Chemical Handbook), 3rd revised edition, Basic Edition II, edited by the Chemical Society of Japan, published by Maruzen Co., Ltd. may be referred. A releasing agent disclosed in JP-A-2002-265636 may also be preferably used. The descriptions contain various preferred examples of not only the releasing agent but also the using method and characteristics thereof, which may be preferably used in the nucleic acid-adsorbing solid carrier of the invention.

The nucleic acid-adsorbing solid carrier may contain a coloring agent. Examples of the coloring agent include organic, inorganic and organic/inorganic complex colorants having been known in the art, such as a colorant, a dye, a pigment, an oxidation coloring colorant, a reduction coloring colorant, a pH indicator, a fluorescent colorant, a coupling colorant, an ultraviolet ray absorbing colorant, an infrared ray absorbing colorant, a near infrared ray absorbing colorant, a pressure-sensitive colorant, a photochromic colorant, a thermochromic colorant, an electrochromic colorant, an organic luminescent colorant, an organic non-linear optical colorant, a chemical luminescent colorant, a medical colorant, a medical diagnostic colorant, a cosmetic colorant, a semiconductor laser colorant, a sublimation transfer colorant, a melt transfer colorant, a thermosensitive colorant, a leuco colorant, an electromagnetic wave-absorbing colorant, a photoconductive colorant and an electrostatic colorant, which may be used solely or in combination of plural kinds thereof in a desired concentration, and they may also be used with a dispersant, such as a surfactant and a protective polymer, in a desired concentration, but the invention is not limited thereto.

The nucleic acid-adsorbing solid carrier may contain a reinforcing agent for improving the membrane strength. Preferred examples of the reinforcing agent include glass fibers, carbon fibers, silicon fibers, cellulose fibers, pulp fibers, potassium titanate fibers, silicon carbide whiskers, basic magnesium sulfate and fibrous zonolite, potassium titanate whiskers, silicon carbide (SiC) whiskers, and calcium carbonate in a whisker form, but the invention is not limited thereto, and any material in a fibrous form or a acicular crystal form may be used. A synthetic polymer may be added for improving the flexural strength. Polyurethane disclosed in JP-A-54-11081 can be preferably used, but the invention is not limited thereto.

The nucleic acid-adsorbing solid carrier may contain a crosslinking agent. As the crosslinking agent, known materials may be used, and it is preferred to select an appropriate species depending on the functional group of the material of the solid carrier. In the case where the functional group is a hydroxyl group, crosslinking agents disclosed in JP-A-7-256066 and JP-A-3-68431 can be preferably used, but the invention is not limited thereto.

The nucleic acid-adsorbing solid carrier may contain a moistening agent. Preferred examples of the moistening agent include those disclosed in JP-A-63-262550, JP-A-63-262549 and JP-B-55-31418, but the invention is not limited thereto.

The nucleic acid-adsorbing porous membrane capable of transmitting a solution therethrough and generally has a thickness of from 10 to 500 μm, and more preferably from 50 to 250 μm. The thickness is preferably as thin as possible from the standpoint of easiness in rinsing.

The nucleic acid-adsorbing porous membrane capable of transmitting a solution therethrough generally has a minimum pore diameter of 0.22 μm or more, and more preferably 0.5 μm or more. The nucleic acid-adsorbing porous membrane capable of transmitting a solution therethrough preferably has a ratio of the maximum pore diameter to the minimum pore diameter of 2 or more. According to the constitution, such a surface area can be obtained that is sufficient for adsorbing a nucleic acid, and the membrane can be prevented from being clogged. More preferably, the ratio of the maximum pore diameter to the minimum pore diameter is 5 or more.

The nucleic acid-adsorbing porous membrane capable of transmitting a solution therethrough generally has a porosity of from 50 to 95%, and preferably from 65 to 80%. The nucleic acid-adsorbing porous membrane capable of transmitting a solution therethrough generally has a bubble point of from 0.1 to 10 $kgf/cm^2$, and preferably from 0.2 to 4 $kgf/cm^2$.

As the nucleic acid-adsorbing porous membrane capable of transmitting a solution therethrough, such a porous membrane is preferably used that has a pressure loss of from 0.1 to 100 kPa. According to the constitution, a uniform pressure can be obtained upon application of pressure. More preferably, such a porous membrane can be used that has a pressure loss of from 0.5 to 50 kPa. The pressure loss referred herein is a minimum pressure necessary for transmitting water per 100 μm in terms of thickness of the membrane.

As the nucleic acid-adsorbing porous membrane capable of transmitting a solution therethrough, such a porous membrane can be used that has a water penetration amount upon transmitting water at a pressure of 1 $kg/cm^2$ at 25° C. of from 1 to 5,000 mL per 1 minute and 1 $cm^2$ of the membrane, and more preferably such a porous membrane can be used that has a water penetration amount upon transmitting water at a pressure of 1 $kg/cm^2$ at 25° C. of from 5 to 1,000 mL per 1 minute and 1 $cm^2$ of the membrane.

As the nucleic acid-adsorbing porous membrane capable of transmitting a solution therethrough, such a porous membrane is preferably used that has an adsorption amount of a nucleic acid of 0.1 μg or more per 1 mg of the porous membrane, and such a porous membrane is more preferably used that has an adsorption amount of a nucleic acid of 0.9 μg or more per 1 mg of the porous membrane.

As the nucleic acid-adsorbing porous membrane capable of transmitting a solution therethrough, such a porous membrane is preferably used that is formed of a cellulose derivative and is not dissolved within 1 hour, but is dissolved within 48 hours upon immersing the porous membrane of 5 mm square in 5 mL of trifluoroacetic acid. Such a membrane is also preferably used that is formed of a cellulose derivative and is dissolved within 1 hour upon immersing the porous membrane of 5 mm square in 5 mL of trifluoroacetic acid, but is not dissolved within 24 hours upon immersing in 5 mL of dichloromethane.

Upon transmitting a sample solution containing a nucleic acid through the nucleic acid-adsorbing porous membrane, it is preferred that the sample solution is transmitted from one surface of the membrane to the other surface thereof from the standpoint that the sample solution can be uniformly made in contact with the porous membrane. Upon transmitting a sample solution containing a nucleic acid through the nucleic acid-adsorbing porous membrane, it is preferred that the sample solution is transmitted from the side having a larger pore diameter to the side having a smaller pore diameter from the standpoint that the membrane is prevented from being clogged.

Upon transmitting a sample solution containing a nucleic acid through the nucleic acid-adsorbing porous membrane, the flow rate of the solution is preferably from 2 to 1,500 μL/sec per 1 $cm^2$ of the membrane for obtaining a suitable contact time of the solution with the porous membrane. In the case where the contact time of the solution to the porous membrane is too small, sufficient separation and purification effect may not be obtained, and a too large contact time is not preferred from the standpoint of operationality. The flow rate is more preferably from 5 to 700 μL/sec per 1 $cm^2$ of the membrane.

The nucleic acid-adsorbing porous membrane capable of transmitting a solution therethrough may be a single membrane, or plural membranes may be used. The plural nucleic acid-adsorbing porous membranes may be the same as or different from each other.

A cartridge for separation and purification of a nucleic acid produced by housing the nucleic acid-adsorbing porous membrane capable of transmitting a solution therethrough can be preferably used. A cartridge for separation and purification of a nucleic acid produced by housing a plurality of the nucleic acid-adsorbing porous membranes capable of transmitting a solution therethrough can also be preferably used. In this case, the plural nucleic acid-adsorbing porous membranes housed in the vessel having at least two openings may be the same as or different from each other.

The plural nucleic acid-adsorbing porous membranes may be a combination of the nucleic acid-adsorbing porous membrane of an inorganic material and the nucleic acid-adsorbing porous membrane of an organic material. Examples thereof include a combination of a glass filter and a porous membrane of regenerated cellulose. The plural nucleic acid-adsorbing porous membranes may be a combination of the nucleic acid-adsorbing porous membrane of an inorganic material and a nucleic acid-non-adsorbing porous membrane of an organic material. Examples thereof include a combination of a glass filter and a porous membrane of nylon or polysulfone The nucleic acid-adsorbing porous membrane having been described hereinabove may have other forms than a membrane depending on the shape of the cartridge. For example, it may have a chip form or a block form.

The cartridge for separation and purification of a nucleic acid may further contain, in the vessel having at least two openings, other members than the nucleic acid-adsorbing porous membrane capable of transmitting a solution therethrough. Examples of the material of the vessel include such plastics as polypropylene, polystyrene, polycarbonate and polyvinyl chloride. A biodegradable material is also preferably used. The vessel may be transparent or may be colored.

The cartridge for separation and purification of a nucleic acid may be equipped with a means for discriminating the individual cartridges for separation and purification of a nucleic acid. Examples of the means for discriminating the individual cartridges for separation and purification of a nucleic acid include a bar code and a magnetic tape.

The cartridge for separation and purification of a nucleic acid may have such a mechanism that facilitate takeoff of the nucleic acid-adsorbing porous membrane from the vessel having at least two openings.

A nucleic acid can be separated and purified by using the cartridge for separation and purification of a nucleic acid having housed therein the nucleic acid-adsorbing porous membrane capable of transmitting a solution therethrough, in the manner containing the following steps, i.e., (a) a step of injecting a sample solution containing a nucleic acid into one opening of the cartridge for separation and purification of a nucleic acid produced by housing the nucleic acid-adsorbing porous membrane capable of transmitting a solution therethrough in the vessel having at least two openings, (b) a step of pressurizing the interior of the cartridge for separation and purification of a nucleic acid by using a pressure difference generating apparatus connected to the one opening of the cartridge for separation and purification of a nucleic acid, so as to pass the sample solution containing a nucleic acid through the nucleic acid-adsorbing porous membrane and to discharge from the other opening of the cartridge for separation and purification of a nucleic acid, whereby the nucleic acid is adsorbed in the nucleic acid-adsorbing porous membrane, (c) a step of injecting a rinsing solution to the one opening of the cartridge for separation and purification of a nucleic acid, (d) a step of pressurizing the interior of the cartridge for separation and purification of a nucleic acid by using a pressure difference generating apparatus connected to the one opening of the cartridge for separation and purification of a nucleic acid, so as to pass the rinsing solution through the nucleic acid-adsorbing porous membrane and to discharge from the other opening of the cartridge for separation and purification of a nucleic acid, whereby the nucleic acid-adsorbing porous membrane having the nucleic acid adsorbed therein is rinsed, (e) a step of injecting a recovering solution to the one opening of the cartridge for separation and purification of a nucleic acid, and (f) a step of pressurizing the interior of the cartridge for separation and purification of a nucleic acid by using a pressure difference generating apparatus connected to the one opening of the cartridge for separation and purification of a nucleic acid, so as to pass the recovering solution through the nucleic acid-adsorbing porous membrane and to discharge from the other opening of the cartridge for separation and purification of a nucleic acid, whereby the nucleic acid is desorbed from the nucleic acid-adsorbing porous membrane and discharged to the outside of the cartridge for separation and purification of a nucleic acid.

In the steps (b), (d) and (f), the sample solution containing a nucleic acid, the rinsing solution or the recovering solution is passed through the nucleic acid-adsorbing porous membrane under the pressurized condition, and more preferably, in the steps (b), (d) and (f), the sample solution containing a nucleic acid, the rinsing solution or the recovering solution is injected to the one opening of the cartridge for separation and purification of a nucleic acid produced by housing the nucleic acid-adsorbing porous membrane capable of transmitting a solution therethrough in the vessel having at least two openings, the interior of the cartridge is pressurized by using a pressure difference generating apparatus connected to the one opening of the cartridge, so as to pass the solution thus injected and to discharge from the other opening. The sample solution containing a nucleic acid, the rinsing solution or the recovering solution is passed through the porous membrane under the pressurized condition, whereby the apparatus can be favorably miniaturized and automated. The pressurizing operation is preferably carried out at a pressure of about from 10 to 200 kPa, and more preferably about from 40 to 100 kPa.

In the aforementioned process for separation and purification of a nucleic acid, the steps of from the first injection of a sample solution containing a nucleic acid to the last step of obtaining the nucleic acid outside the cartridge for separation and purification of a nucleic acid can be completed within 10 minutes, and under favorable conditions within 2 minutes. In the process for separation and purification of a nucleic acid, the nucleic acid can be recovered at a yield of 50% by mass or more based on the total amount of the nucleic acid contained in the sample, and under favorable conditions 90% by mass or more.

In the process for separation and purification of a nucleic acid, such a nucleic acid can be recovered that has a wide range of molecular weight, such as from 1 to 200 kbp, and particularly from 20 to 140 kbp. In other words, a nucleic acid having a longer chain can be recovered in comparison to the spin column method using a glass filter having been conventionally practiced.

In the process for separation and purification of a nucleic acid, such a nucleic acid can be recovered that has a purity of a measured value with an ultraviolet and visible spectrophotometer (260 nm/280 nm) of from 1.6 to 2.0 for DNA and from 1.8 to 2.2 for RNA, and thus a nucleic acid having high purity with a small amount of impurities can be steadily obtained. Furthermore, such a nucleic acid can be recovered that has a purity of a measured value with an ultraviolet and visible spectrophotometer (260 nm/280 nm) of around 1.8 for DNA and around 2.0 for RNA.

The sample measured in the invention is not particularly limited, and in the diagnostic field, solutions prepared from biomaterials are measured, such as a biological fluid collected as an analyte, e.g., whole blood, blood plasma, blood serum, urine, faeces, semen and saliva, a plant (or a part thereof), an animal (or a part thereof), a bacterium, a virus, and a dissolved product or a homogenate thereof.

The analyte is then treated with an aqueous solution containing a reagent capable of dissolving a cell membrane and a nuclear membrane to solubilize a nucleic acid (a nucleic acid solubilizing reagent). According to the treatment, a cell membrane and a nuclear membrane are dissolved to disperse a nucleic acid in the aqueous solution, whereby a sample solution containing a nucleic acid is obtained.

Upon dissolving a cell membrane and a nuclear membrane to solubilize a nucleic acid, in the case where a sample to be analyzed is whole blood, for example, the following steps are required, i.e., (1) removal of erythrocytes, (2) removal of various proteins, and (3) dissolution of leukocytes and dissolution of a nuclear membrane. The step (1) of removal of erythrocytes and the step (2) of removal of various proteins are required for preventing the porous membrane from suffering nonspecific adsorption and clogging, and the step (3) of dissolution of leukocytes and dissolution of a nuclear membrane is required for solubilizing a nucleic acid, which is the target of extraction. In particular, the step (3) of dissolution of leukocytes and dissolution of a nuclear membrane is an important step, and in the process of the invention, it is necessary that a nucleic acid is solubilized in this step.

The analyte containing a nucleic acid may be an analyte containing a sole nucleic acid or an analyte containing plural different kinds of nucleic acid. The species of a nucleic acid to be recovered is not particularly limited and includes DNA and RNA. The number of the analyte may be one or a plurality (plural analytes may be processed in parallel to each other by using plural vessels). The length of a nucleic acid to be recovered is also not particularly limited, and for example, a nucleic acid having an arbitrary length of from several bp to several Mbp can be used. The length of a nucleic acid is generally from several bp to several hundreds kbp from the standpoint of operation. In the method of separation and purification of a nucleic acid according to the invention, a nucleic acid having a relatively larger length can be rapidly recovered in comparison to the conventional simple method of separation and purification of a nucleic acid, and a nucleic acid having a length of 50 kbp or more can be preferably recovered, more preferably 70 kbp or more, and further preferably 100 kbp or more. It is preferred that operations of stirring and pipetting are gently carried out for recovering DNA having a larger length.

The process of dissolving a cell membrane and a nuclear membrane, solubilizing a nucleic acid, and obtaining a sample solution containing a nucleic acid from an analyte will be described. In the invention, a nucleic acid solubilizing reagent is used for dissolving a cell membrane and a nuclear membrane to solubilize a nucleic acid. Examples of the nucleic acid solubilizing reagent include a solution containing a compound selected from a chaotropic agent, a surfactant, a defoaming agent, a protease, and a nucleic acid stabilizing agent.

The process for dissolving a cell membrane and a nuclear membrane and solubilizing a nucleic acid to obtain a sample solution containing a nucleic acid from an analyte includes (I) a step of injecting an analyte containing a cell or a virus in a vessel, (II) a step of adding a nucleic acid solubilizing reagent to the vessel to mix the analyte and the nucleic acid solubilizing reagent, (III) a step of incubating the mixed solution obtained in the preceding step, and (IV) a step of adding a water soluble organic solvent to the mixed solution thus incubated.

In the process for dissolving a cell membrane and a nuclear membrane and solubilizing a nucleic acid to obtain a sample solution containing a nucleic acid from an analyte, the analyte is homogenized to improve the suitability to the automated process. Examples of the homogenizing treatment include an ultrasonic treatment, use of an edged projection, use of a high-speed agitator, extrusion from minute gaps, and a treatment using glass beads.

In the process for dissolving a cell membrane and a nuclear membrane and solubilizing a nucleic acid to obtain a sample solution containing a nucleic acid from an analyte, a nucleic acid solubilizing reagent containing a protease may be used, whereby the recovering amount and the recovering efficiency of a nucleic acid are improved to facilitate reduction of the necessary amount of the analyte containing a nucleic acid and acceleration of the process speed.

Preferred examples of the protease include serine protease, cysteine protease and metal protease, at least one of which may be preferably used. As the protease, a mixture of plural kinds of proteases may be preferably used. The serine protease is not particularly limited, and for example, protease K may be preferably used. The cysteine protease is not particularly limited, and for example, papain and cathepsin may be preferably used. The metal protease is not particularly limited, and for example, carboxy peptidase may be preferably used. The protease is preferably used in a concentration of from 0.001 to 10 IU, and more preferably from 0.01 to 1 IU, per 1 mL of the total amount of the reaction system upon addition of the protease.

As the protease, a protease containing no nuclease is preferably used. A protease containing a stabilizer is preferably used. Preferred examples of the stabilizer include a metallic ion. Specifically, a magnesium ion is preferably used, which may be added, for example, in the form of magnesium chloride. The addition of the stabilizer to the protease reduces the amount of the protease necessary for recovering a nucleic acid, which reduces the cost for recovering a nucleic acid. The stabilizer for a protease is preferably contained in a concentration of from 1 to 1,000 mM, and more preferably from 10 to 100 mM, based on the total amount of the reaction system.

The protease may be used for recovering a nucleic acid as one reagent obtained by mixing beforehand with the other reagent, such as a chaotropic salt and a surfactant. The protease may be used as two or more reagents separately from the other reagent, such as a chaotropic salt and a surfactant. In the later case, a reagent containing the protease is firstly mixed with an analyte, and then a reagent containing a chaotropic salt and a surfactant is mixed therewith. It is also possible that a reagent containing a chaotropic salt and a surfactant is firstly mixed, and then a reagent containing the protease is mixed. Alternatively, the protease may be added dropwise from a protease storage container to a mixed solution of an analyte and a reagent containing a chaotropic salt and a surfactant. In this case, the operation can be simplified.

The concentration of a chaotropic salt in the nucleic acid solubilizing reagent is preferably 0.5 M or more, more preferably from 0.5 to 4 M, and further preferably from 1 to 3 M. As the chaotropic salt, guaridine hydrochloride is preferred, and other chaotropic salts may also be used, such as guanidine isothiocyanate, guanidine thiocyanate, urea, a guanidine salt, sodium isothiocyanate, sodium iodide and potassium iodide).

Examples of the surfactant include a nonionic surfactant, a cationic surfactant, an anionic surfactant and an amphoteric surfactant. In the invention, a nonionic surfactant is preferably used. Examples of the nonionic surfactant include a polyoxyethylene alkyl phenyl ether surfactant, a polyoxyethylene alkyl ether surfactant, and a fatty acid alkanol amide surfactant, and a polyoxyethylene alkyl ether surfactant is preferably used. More preferred examples thereof include polyoxyethylene alkyl ether surfactants selected from POE decyl ether, POE lauryl ether, POE tridecyl ether, POE alkylene decyl ether, POE sorbitan monolaurate, POE sorbitan monooleate, POE sorbitan monostearate, polyoxyethylene sorbit tetraoleate, POE alkylamine and POE acetylene glycol.

A cationic surfactant is also preferably used. More preferred examples of the cationic surfactant include cationic surfactants selected from cetyltrimethylammonium chloride, tridecyltrimethylammonium chloride, tetradecyltrimethylammonium chloride and cetylpyridinium chloride.

The surfactant may be used solely or in combination of plural kinds thereof. The concentration of the surfactant in the nucleic acid solubilizing reagent is preferably from 0.1 to 20% by mass.

In the case where a nucleic acid other than RNA, e.g., DNA, is recovered, a ribonuclease is preferably added to a nucleic acid solubilizing reagent in the step of dissolving a cell membrane and a nuclear membrane and solubilizing a nucleic acid to obtain a sample solution containing a nucleic acid from an analyte. In this case, interference by RNA remaining in the recovered nucleic acid can be reduced. It is also preferred to add a deoxyribonuclease inhibitor. In the case where a nucleic acid other than DNA, e.g., RNA, is recovered, on the other hand, a deoxyribonuclease is preferably added to a nucleic acid solubilizing reagent. In this case, interference by DNA remaining in the recovered nucleic acid can be reduced. It is also preferred to add a ribonuclease inhibitor. As the ribonuclease inhibitor, one capable of inhibiting specifically a ribonuclease. The ribonuclease is not particularly limited, and for example, a degradative enzyme capable of decomposing specifically RNA, such as ribonuclease H (RNase H), can be preferably used. The deoxyribonuclease is not particularly limited, and for example, a degradative enzyme capable of decomposing specifically DNA, such as DNase I, can be preferably used. The nuclease and the nuclease inhibitor can be used in concentrations that are ordinarily employed. A heating treatment may be carried out in the ordinary manner. The heating treatment is preferably carried out simultaneously with the treatment with a protease.

Examples of the nucleic acid stabilizer include those having a function of deactivating the activity of a nuclease. Some kinds of analytes contain a nuclease decomposing a nucleic acid, and upon homogenizing a nucleic acid, the nuclease acts on the nucleic acid to reduce the yield in some cases. The nucleic acid stabilizer stabilize the presence of a nucleic acid in an analyte, whereby the recovered amount and the recovered efficiency of a nucleic acid are favorably improved to facilitate reduction of the necessary amount of the analyte and acceleration of the process speed.

As the nucleic acid stabilizer having a function of deactivating the activity of a nuclease, a compound that is generally used as a reducing agent can be used. Examples of the reducing agent include hydrogen, a hydrogen compound, such as hydrogen iodide, hydrogen sulfide, aluminum lithium hydride and boron sodium hydride, a metal having a large electric positive property, such as an alkali metal, magnesium, calcium aluminum and zinc, amalgam of these metals, an aldehyde compound, a saccharide, an organic acid, such as formic acid and oxalic acid, and a mercapto compound. Among these, a mercapto compound is preferred. Examples of the mercapto compound include N-acetylcysteine, mercaptoethanol and alkylmercaptan. In particular, β-mercaptoethanol is preferred. The mercapto compound may be used solely or in combination of plural kinds thereof.

The nucleic acid stabilizer is preferably used in the pretreating solution in a concentration of from 0.1 to 20% by mass, and more preferably from 0.3 to 15% by mass. The mercapto compound is preferably used in the pretreating solution in a concentration of from 0.1 to 10% by mass, and more preferably from 0.5 to 5% by mass.

In the process for dissolving a cell membrane and a nuclear membrane and solubilizing a nucleic acid to obtain a sample solution containing a nucleic acid from an analyte, the sample solution containing a nucleic acid preferably contains a defoaming agent. Preferred examples of the defoaming agent include a silicone defoaming agent and an alcohol defoaming agent, and preferred examples of the alcohol defoaming agent include an acetylene glycol surfactant.

Specific examples of the defoaming agent include a silicone defoaming agent (such as a silicone oil, dimethylpolysiloxane, a silicone emulsion, modified polysiloxane and a silicone compound), an alcohol defoaming agent (such as acetylene glycol, heptanol, ethylhexanol, a higher alcohol and polyoxyalkylene glycol), an ether defoaming agent (such as heptylcellosolve and nonylcellosolve-3-heptylcorbitol), a fat or oil defoaming agent (such as animal and vegetable oils), a fatty acid defoaming agent (such as stearic acid, oleic acid and palmitic acid), a metallic soap defoaming agent (such as aluminum stearate and calcium stearate), a fatty acid ester defoaming agent (such as natural wax and tributyl phosphate), a phosphate ester defoaming agent (such as sodium octylphosphate), an amine defoaming agent (such as diamylamine), an amide defoaming agent (such as stearic acid amide), and other defoaming agents (such as ferric sulfide and bauxite). It is particularly preferred that two components of a silicone defoaming agent and an alcohol defoaming agent are used in combination. As the alcohol defoaming agent, an acetylene glycol surfactant is preferably used.

The nucleic acid solubilizing reagent is also preferably supplied in a dried state. A container that contains in advance a dried (for example, freeze-dried) protease may be employed. The sample solution containing a nucleic acid can be obtained by using both the nucleic acid solubilizing reagent supplied in a dried state and the dried protease. In the case where the sample solution containing a nucleic acid is obtained in the aforementioned method, the nucleic acid solubilizing reagent and the protease are improved in storage stability, which simplifies the operation without change in yield of a nucleic acid.

The method for mixing the analyte with the nucleic acid solubilizing reagent is not particularly limited. They are preferably mixed with a stirring device at a rate of from 30 to 3,000 rpm for a period of from 1 second to 3 minutes. According to the operation, the yield of a nucleic acid to be separated and purified can be increased. They are also preferably mixed by rollover mixing in 5 to 30 times. They may also be mixed by a pipetting operation in 10 to 50 times. In this case, the yield of a nucleic acid to be separated and purified can be increased by a simple operation.

In the case where the nucleic acid solubilizing reagent containing a protease is used, a mixed solution of an analyte and the nucleic acid solubilizing reagent may be incubated at the optimal temperature and reaction time of the protease to increase the yield of a nucleic acid to be separated and purified. The incubation temperature is generally from 20 to 70° C., and preferably the optimal temperature of the protease, and the incubation time is generally from 1 minute to 18 hours, and preferably the optimal time of the protease. The incubation method is not particularly limited, and can be carried out by placing in a hot water bath or a heating oven.

In the process for dissolving a cell membrane and a nuclear membrane and solubilizing a nucleic acid to obtain a sample solution containing a nucleic acid from an analyte, preferred examples of the water soluble organic solvent added to the incubated mixture include an alcohol, acetone, acetonitrile and dimethylformamide. In particular, an alcohol is preferably used.

The alcohol may be either a primary alcohol, a secondary alcohol or a tertiary alcohol. Preferred examples of the alcohol include methyl alcohol, ethyl alcohol, propyl alcohol and an isomer thereof, and butyl alcohol and an isomer thereof, and ethanol is more preferably used. The water soluble organic solvent may be used solely or in combination of plural kinds thereof. The concentration of the water soluble organic solvent in the nucleic acid solubilizing reagent is preferably from 1 to 20% by mass. The final concentration of the water soluble organic solvent in the sample solution containing a nucleic acid is preferably from 5 to 90% by mass.

In the process for dissolving a cell membrane and a nuclear membrane and solubilizing a nucleic acid to obtain a sample solution containing a nucleic acid from an analyte, the sample solution preferably has pH of from 5 to 10, more preferably pH of from 6 to 9, and further preferably pH of from 7 to 8.

In the process for dissolving a cell membrane and a nuclear membrane and solubilizing a nucleic acid to obtain a sample solution containing a nucleic acid from an analyte, the resulting sample solution containing a nucleic acid preferably has a surface tension of 0.05 J/m$^2$ or less, a viscosity of from 1 to 10,000 mPa, and a specific gravity of from 0.8 to 1.2.

The rinsing step will be described below. The recovered amount and the purity of a nucleic acid are improved by rinsing, whereby the necessary amount of the analyte containing a nucleic acid can be reduced. The rinsing step may be only a single operation of rinsing for speeding up the process, and in the case where the purity is an important factor, the rinsing operation is preferably repeated in plural times.

In the rinsing step, a rinsing solution is supplied to the cartridge for separation and purification of a nucleic acid having the nucleic acid-adsorbing porous membrane housed therein by using an automatic injecting device or a supplying means having a function equivalent thereto. The rinsing solution may be supplied from one opening of the cartridge for separation and purification of a nucleic acid (i.e., the opening, from which the sample solution containing a nucleic acid is injected), and the interior of the cartridge for separation and purification of a nucleic acid may be pressurized by using a pressure difference generating apparatus connected to the one opening to pass the rinsing solution through the nucleic acid-adsorbing porous membrane and to discharge from the other opening. The rinsing solution may be supplied from the one opening and then discharged from the same opening. Furthermore, the rinsing solution may be supplied from the other opening than the one opening, from which the sample solution containing a nucleic acid is injected, and then discharged from the same other opening. It is preferred to employ such a method that the rinsing solution is supplied from one opening of the cartridge for separation and purification of a nucleic acid, and then passed through the nucleic acid-adsorbing porous membrane and to discharge from the other opening than the one opening owing to excellent rinsing efficiency obtained thereby. The amount of the rinsing solution in the rinsing step is preferably 2 µL/mm$^2$ or more. While a larger amount of the rinsing solution improves the rinsing efficiency, the amount is preferably 200 µL/mm$^2$ or less for maintaining the operationality and for preventing the sample from flowing out.

The flow rate upon passing the rinsing solution through the nucleic acid-adsorbing porous membrane in the rinsing step is preferably from 2 to 1,500 µL/sec, and more preferably from 5 to 700 µL/sec, per unit area (cm$^2$) of the membrane. The rinsing operation can be sufficiently carried out by decreasing the flow rate to take a prolonged period of time, but the aforementioned range is preferably employed since it is important that the separation and purification operation of a nucleic acid is speeded up.

In the rinsing step, the temperature of the rinsing solution is preferably from 4 to 70° C., and is more preferably room temperature. In the rinsing step, the rinsing operation can be carried out while the cartridge for separation and purification of a nucleic acid is subjected to centrifugal separation under application of mechanical vibration or agitation with ultrasonic wave to the cartridge.

In the rinsing step, the rinsing solution generally does not contain an enzyme, such as a nuclease, but may contain such an enzyme that decomposes impurities, such as proteins. In some cases, a deoxyribonuclease or a ribonuclease may be contained. By using a rinsing solution containing a deoxyribonuclease, only RNA can be selectively recovered from an analyte. By using a rinsing solution containing a ribonuclease, on the other hand, only DNA can be selectively recovered from an analyte.

In the rinsing step, the rinsing solution is preferably a solution containing a water soluble organic solvent and/or a water soluble salt. The rinsing solution necessarily has such a function that rinses out impurities in the sample solution that are adsorbed in the nucleic acid-adsorbing porous membrane along with a nucleic acid. In order to attain the function, it is necessary that the rinsing solution has such a composition that a nucleic acid is not desorbed from the nucleic acid-adsorbing porous membrane, but the impurities are desorbed therefrom. For the purpose, a water soluble organic solvent, such as an alcohol, is suitable for desorbing the other components than a nucleic acid because a nucleic acid has poor solubility in the water soluble organic solvent. The addition of a water soluble salt improves the adsorption efficiency of a nucleic acid to improve the function of selective removal of the unnecessary components.

Examples of the water soluble organic solvent contained in the rinsing solution include methanol, ethanol, isopropanol, n-propanol, butanol and acetone, and among these, ethanol is preferably used. The amount of the water soluble organic solvent contained in the rinsing solution is preferably from 20 to 100% by weight, and more preferably from 40 to 80% by weight.

The water soluble salt contained in the rinsing solution is preferably a salt of a halide, and a chloride is more preferred. The water soluble salt is preferably a monovalent or divalent cation, and more preferably, an alkali metal salt or an alkaline earth metal salt, with a sodium salt and potassium salt being particularly preferred among them. In the case where the water soluble salt is contained in the rinsing solution, the concentration thereof is preferably 10 mmole/L or more, and the upper limit thereof is not particularly limited as far as the solubility of impurities is not impaired, and is preferably 1 mole/L or less, and more preferably 0.1 mole/L or less. It is particularly preferred that the water soluble salt is sodium chloride, and sodium chloride is contained in a concentration of 20 mmole/L or more.

The rinsing solution preferably does not contain chaotropic substance, whereby such a possibility can be reduced that a chaotropic substance is mixed therein in the recovering step subsequent to the rinsing step. In the case where a chaotropic substance is mixed in the recovering step, the enzyme reaction, such as PCR, is often impaired, and therefore, it is ideal that the rinsing solution contains no chaotropic substance in consideration of the enzyme reaction. A chaotropic substance is corrosive and harmful, and therefore, the disuse of a chaotropic substance is significantly advantageous to safety in experimental operation by an operator. The chaotropic substance referred herein includes urea, a guanidine salt, sodium isothiocyanate, sodium iodide and potassium iodide, as described hereinabove.

In a rinsing step in a process of separation and purification of a nucleic acid according to the conventional technique, a rinsing solution often remains in a vessel, such as a cartridge, since the vessel has high wettability to the rinsing solution, and the rinsing solution is mixed into a subsequent recovering step to cause reduction in purity of a nucleic acid and reduction in reactivity in the subsequent step. Therefore, in the case where a vessel, such as a cartridge, is used upon adsorption and desorption of a nucleic acid, it is important that a solution used for rinsing, particularly a rinsing solution, is prevented from remaining in the cartridge to avoid adverse affect on the subsequent step.

Accordingly, in order to prevent the rinsing solution in the rinsing step from being mixed in the recovering step as the subsequent step to reduce the amount of the rinsing solution remaining in the cartridge to the minimum value, the rinsing solution preferably has a surface tension of less than 0.035 $J/m^2$. The reduction in surface tension improves the wettability between the rinsing solution and the cartridge to suppress the amount of the solution remaining.

On the other hand, it is also possible that in order to reduce the remaining amount of the rinsing solution used in the rinsing step, the surface tension of the rinsing solution is made 0.035 $J/m^2$ or more to facilitate running off of droplets of the rinsing solution, whereby the amount of the solution remaining is reduced. The surface tension can be selected depending on the combination of the porous membrane having a nucleic acid adsorbed therein, the recovering solution and the rinsing solution.

The rinsing step can be simplified by using the nucleic acid-adsorbing porous membrane of the invention, i.e., (1) it is sufficient that the rinsing solution is passed through the nucleic acid-adsorbing porous membrane only one time, (2) the rinsing step can be carried out at room temperature, (3) the recovering solution can be injected to the cartridge immediately after rinsing, and (4) one, or two or more of the advantages (1), (2) and (3) can be conducted. This is because in the conventional technique, a drying step is often necessary for removing rapidly an organic solvent contained in a rinsing solution, but the drying step can be omitted in the invention since the nucleic acid-adsorbing porous membrane of the invention is in a form of a thin membrane.

There has been such a problem that in the rinsing step of the process of separation and purification of a nucleic acid, a rinsing solution is scattered and attached to the environments to contaminate a sample. The contamination of this kind in the rinsing step can be suppressed from occurring by modifying the shapes of the cartridge for separation and purification of a nucleic acid having the nucleic acid-adsorbing porous membrane housed in the vessel having two openings and the waste liquor container.

A step of recovering a nucleic acid by desorbing from the nucleic acid-adsorbing porous membrane will be described. In the recovering step, a recovering solution is supplied to the cartridge for separation and purification of a nucleic acid having the nucleic acid-adsorbing porous membrane housed therein by using an automatic injecting device or a supplying means having a function equivalent thereto. The recovering solution may be supplied from one opening of the cartridge for separation and purification of a nucleic acid (i.e., the opening, from which the sample solution containing a nucleic acid is injected), and the interior of the cartridge for separation and purification of a nucleic acid may be pressurized by using a pressure difference generating apparatus connected to the one opening to pass the recovering solution through the nucleic acid-adsorbing porous membrane and to discharge from the other opening. The recovering solution may be supplied from the one opening and then discharged from the same opening. Furthermore, the recovering solution may be supplied from the other opening than the one opening, from which the sample solution containing a nucleic acid is injected, and then discharged from the same other opening. It is preferred to employ such a method that the recovering solution is supplied from one opening of the cartridge for separation and purification of a nucleic acid, and then passed through the nucleic acid-adsorbing porous membrane and to discharge from the other opening than the one opening owing to excellent recovering efficiency obtained thereby.

The desorption of a nucleic acid can be carried out by adjusting the volume of the recovering solution with respect to the volume of the sample solution containing the nucleic acid prepared from an analyte. The amount of the recovering solution containing the nucleic acid thus separated and purified depends on the amount of the analyte used. The amount of the recovering solution that is ordinarily employed is from several tens to several hundreds μL, and in the case where the amount of the analyte is considerably small, or in the case where a large amount of a nucleic acid is to be separated and purified, the amount of the recovering solution may vary from 1 μL to several tens mL.

Preferred examples of the recovering solution include distilled water and a Tris/EDTA buffer. In the case where a nucleic acid thus recovered is subjected to PCR (polymerase chain reaction), a buffer solution used in the PCR (for example, an aqueous solution having final concentrations of KCl 50 mmole/L, Tris-CL 10 mmole/L and $MgCl_2$ 1.5 mmole/L) may be used.

The recovering solution preferably has pH of from 2 to 11, and more preferably pH of from 5 to 9. In particular, the ion strength and the salt concentration thereof influence on elution of the adsorbed nucleic acid. The recovering solution preferably has an ion strength of 290 mmole/L or less and a salt concentration of 90 mmole/L or less. According to the constitution, the recovering rate of a nucleic acid is improved to recover a larger amount of a nucleic acid. The nucleic acid to be recovered may be single-strand or duplex.

By reducing the volume of the recovering solution in comparison to the volume of the initial sample solution containing a nucleic acid, the recovering solution containing the nucleic acid in an increased concentration can be obtained. The ratio of the volume of the recovering solution to the volume of the sample solution (recovering solution/sample solution) is preferably 1/100 to 99/100, and more preferably from 1/10 to 9/10. According to the constitution, the nucleic acid can be easily concentrated without an operation for concentrating the nucleic acid in the process for separation and purification of the nucleic acid. A method of providing a nucleic acid solution containing a nucleic acid in an increased concentration can be provided according to the aforementioned manner.

As another method, it is possible that a nucleic acid is desorbed with the recovering solution in a larger amount than the initial sample solution containing the nucleic acid to obtain the recovering solution having a desired concentration of the nucleic acid, and thus the recovering solution containing the nucleic acid in such a concentration that is suitable for the subsequent step (such as PCR). The ratio of the volume of the recovering solution to the volume of the sample solution (recovering solution/sample solution) is preferably from 1/1 to 50/1, and more preferably from 1/1 to 5/1. According to the constitution, the operation can be simplified by omitting the step of adjusting the concentration after separating and purifying the nucleic acid. Furthermore, by using a sufficiently large amount of the recovering solution, the recovering rate of the nucleic acid from the porous membrane can be improved.

The number of the injection operation of the recovering solution is not particularly limited, and may be only one time or plural times. In general, when a nucleic acid is to be separated and purified in a rapid and simple manner, the recovering operation may be carried out in one time, and when a large amount of a nucleic acid is to be recovered, the recovering solution may be injected in plural times.

In the recovering step, the recovering solution for a nucleic acid may have such a composition that can be used in the subsequent step. A nucleic acid thus separated and purified is often amplified by the PCR (polymerase chain reaction) method. In this case, it is necessary that the nucleic acid solution thus separated and purified is diluted with a buffer solution suitable for the PCR method. In the case where a buffer solution suitable for the PCR method is used in the recovering step of the process herein, the operation can be transferred to the subsequent PCR method easily and rapidly.

In the recovering step, the recovering solution may contain a stabilizer for preventing the recovered nucleic acid from being decomposed. Examples of the stabilizer that may be added include an antibacterial agent, antifungal agent and an inhibitor of nucleic acid decomposition. Examples of the inhibitor of nucleic acid decomposition include EDTA. The stabilizer may be added to the recovering container in advance.

The recovering container used in the recovering step is not particularly limited, and a recovering container produced with a material having no absorption at 260 nm can be used. In this case, the concentration of the recovered nucleic acid solution can be measured without transfer to another container. Examples of the material having no absorption at 260 nm include quartz glass, but the invention is not limited thereto.

INDUSTRIAL APPLICABILITY

According to the invention, such a cartridge retaining mechanism for a nucleic acid extracting apparatus can be provided that can retain airtightness upon pressurizing without drastic modification of the constitution of the nucleic acid extracting apparatus.

The entire disclosure of each and every foreign patent application from which the benefit of foreign priority has been claimed in the present application is incorporated herein by reference, as if fully set forth.

The invention claimed is:

1. A cartridge retaining mechanism equipped in a nucleic acid extracting apparatus for extracting a nucleic acid, the cartridge retaining mechanism comprising:
   a cartridge having a cylindrical shape with a bottom, and the bottom is shaped in a funnel shape;
   a nucleic acid-adsorbing solid carrier that traps a nucleic acid, and the nucleic acid-adsorbing solid carrier is disposed at the bottom of the cartridge; and
   a cartridge retaining member that retains the cartridge,
   wherein the cartridge retaining member comprises: a supporting part that supports the cartridge; and a pressure-proof retaining part that is attached to an open end of the cartridge, and
   wherein the pressure-proof retaining part has a nozzle receiving opening, onto which a pressure nozzle of the nucleic acid extracting apparatus is pressed, and
   wherein the cartridge is retained between the supporting part and the pressure-proof retaining part upon pressing the pressure nozzle onto the nozzle receiving opening.

2. The cartridge retaining mechanism according to claim 1, wherein the pressure-proof retaining part comprises a gasket part, which is in contact with the cartridge upon pressing the pressure nozzle onto the nozzle receiving opening.

3. The cartridge retaining mechanism according to claim 1, wherein the cartridge retaining mechanism further comprises an engaging member that engages the pressure-proof retaining part to the supporting part upon pressing the pressure nozzle onto the nozzle receiving opening.

4. The cartridge retaining mechanism according to claim 1, wherein the supporting part comprises a biasing member that biases the cartridge toward the pressure-proof retaining part.

5. A cartridge retaining mechanism equipped in a nucleic acid extracting apparatus for extracting a nucleic acid, the cartridge retaining mechanism comprising:
   a cartridge having a cylindrical shape with a bottom, and the bottom is shaped in a funnel shape;
   a nucleic acid-adsorbing solid carrier that traps a nucleic acid, and the nucleic acid-adsorbing solid carrier is disposed at the bottom of the cartridge;
   a cartridge retaining member that retains the cartridge; and
   a cap that is detachably mounted on an open end of the cartridge,
   wherein the cartridge retaining member comprises: a supporting part that supports the cartridge; and a pressure-proof retaining part that holds the cap, and
   wherein the pressure-proof retaining part has an opening, through which a pressure nozzle of the nucleic acid extracting apparatus is inserted, and
   the cap has a nozzle receiving opening, onto which the pressure nozzle is pressed, and the nozzle receiving opening is connected to the opening of the pressure-proof retaining part, and
   wherein the cartridge is retained between the supporting part and the pressure-proof retaining part upon pressing the pressure nozzle onto the nozzle receiving opening.

6. The cartridge retaining mechanism according to claim 5, wherein the cap has a fitting part that fits with the cartridge, and the cap comprises a sealing member, which is in contact with the cartridge and equipped in the fitting part.

* * * * *